US011564587B2

(12) United States Patent
Arad

(10) Patent No.: US 11,564,587 B2
(45) Date of Patent: Jan. 31, 2023

(54) PHYSICAL METHODS FOR LIVING TISSUE INACTIVATION AND DETECTION, AND PHYSICAL METHODS IN USE FOR THE DETECTION AND INACTIVATION OF LIVING BODIES (LIKE EBOLA AND 2019 CORONAVIRUS) IN LIVING SYSTEMS AND NON-LIVING SYSTEMS THEREOF

(71) Applicant: Dorit Arad, Tel Aviv (IL)

(72) Inventor: Dorit Arad, Tel Aviv (IL)

( * ) Notice: Subject to any disclaimer, the term of this patent is extended or adjusted under 35 U.S.C. 154(b) by 0 days.

(21) Appl. No.: 17/405,112

(22) Filed: Aug. 18, 2021

(65) Prior Publication Data

US 2021/0378540 A1    Dec. 9, 2021

Related U.S. Application Data

(63) Continuation-in-part of application No. 17/167,291, filed on Feb. 4, 2021, now abandoned.

(60) Provisional application No. 62/970,790, filed on Feb. 6, 2020, provisional application No. 62/970,775, filed on Feb. 6, 2020.

(51) Int. Cl.
| *A61B 5/0531* | (2021.01) |
| *A61B 5/00* | (2006.01) |
| *A61L 2/00* | (2006.01) |
| *A61B 10/00* | (2006.01) |

(52) U.S. Cl.
CPC .......... *A61B 5/0531* (2013.01); *A61B 5/4836* (2013.01); *A61B 5/746* (2013.01); *A61L 2/0029* (2013.01); *A61B 10/0051* (2013.01); *A61B 2560/02* (2013.01); *A61B 2560/04* (2013.01)

(58) Field of Classification Search
None
See application file for complete search history.

(56) References Cited

U.S. PATENT DOCUMENTS

| 4,562,843 | A  | * | 1/1986 | Djordjevich | A61B 5/0205 600/485 |
| 2005/0015017 | A1 | * | 1/2005 | Horne | A61B 5/0531 600/547 |
| 2009/0124924 | A1 | * | 5/2009 | Eror | A61B 5/053 600/547 |
| 2012/0041279 | A1 | * | 2/2012 | Freeman | A61B 5/053 600/301 |
| 2013/0331678 | A1 | * | 12/2013 | Lading | A61B 5/1075 600/393 |
| 2018/0271423 | A1 | * | 9/2018 | Agarwal | A61B 5/0537 |
| 2020/0221969 | A1 |  | 7/2020 | Ram et al. | |
| 2020/0300805 | A1 |  | 9/2020 | Ram et al. | |
| 2020/0300842 | A1 |  | 9/2020 | Ram et al. | |

(Continued)

*Primary Examiner* — Matthew Kremer

(57) ABSTRACT

A system for detecting presence of coronavirus in a subject, the system including a first pad for placing a first hand, the pad including a contact to measure conductance of the subject's body, a conductance meter connected to the contact, a second pad for placing a second hand, a source of electromagnetic radiation for irradiating the second pad.

A system for detecting presence of coronavirus in a subject, the system including a chip with a plurality of wires disposed on or in the chip, a conductance meter arranged to measure conductance between the wires, and biological material associated with the coronavirus disposed on or in the chip.

Related apparatus and methods are also described.

10 Claims, 7 Drawing Sheets

(56) References Cited

U.S. PATENT DOCUMENTS

2020/0303534 A1 9/2020 Ram et al.
2021/0330253 A1* 10/2021 Wright .................. A61B 5/742

* cited by examiner

```
                    ┌─────────────────────────────────────┐
                    │   PROVIDE A BASELINE VALUE OF       │── 252
                    │ CONDUCTANCE OF A SUBJECT'S BODY     │
                    └─────────────────────────────────────┘
                                      │
                                      ▼
                    ┌─────────────────────────────────────┐
                    │   IRRADIATE THE SUBJECT'S BODY WITH │
                    │ ELECTROMAGNETIC RADIATION AT        │── 254
                    │ FREQUENCIES ASSOCIATED WITH THE     │
                    │ CORONAVIRUS                         │
                    └─────────────────────────────────────┘
                                      │
                                      ▼
                    ┌─────────────────────────────────────┐
                    │   MEASURE THE CONDUCTANCE OF THE    │
                    │ SUBJECT'S BODY, THEREBY PROVIDING   │── 256
                    │ A SECOND VALUE OF CONDUCTANCE       │
                    └─────────────────────────────────────┘
                                      │
                                      ▼
                    ┌─────────────────────────────────────┐
                    │       COMPARE THE SECOND VALUE      │── 258
                    │         TO THE BASELINE VALUE       │
                    └─────────────────────────────────────┘
                                      │
                                      ▼
                    ┌─────────────────────────────────────┐
                    │ IF THE SECOND VALUE IS DIFFERENT    │
                    │ FROM THE BASELINE VALUE BY MORE     │
                    │ THAN A THRESHOLD AMOUNT, PRODUCE    │── 260
                    │ AN ALERT THAT THE SUBJECT'S BODY    │
                    │ CARRIES THE CORONAVIRUS             │
                    └─────────────────────────────────────┘
```

FIG. 2E

```
┌─────────────────────────────────────────┐
│ PROVIDE A SYSTEM, THE SYSTEM INCLUDING: │
│   A CHIP WITH A PLURALITY OF WIRES      │
│   DISPOSED ON OR IN THE CHIP;           │──── 402
│   A CONDUCTANCE METER ARRANGED TO       │
│   MEASURE CONDUCTANCE BETWEEN THE WIRES;│
│   AND                                   │
│   BIOLOGICAL MATERIAL ASSOCIATED WITH   │
│   THE CORONAVIRUS DISPOSED ON OR IN THE CHIP │
└─────────────────────────────────────────┘
                    ▼
┌─────────────────────────────────────────┐
│ PROVIDE A BASELINE VALUE OF CONDUCTANCE │──── 404
│ BETWEEN WIRES IN THE CHIP               │
└─────────────────────────────────────────┘
                    ▼
┌─────────────────────────────────────────┐
│ PROVIDE A FLUID SAMPLE TAKEN FROM A SUBJECT │──── 406
└─────────────────────────────────────────┘
                    ▼
┌─────────────────────────────────────────┐
│ DISPOSE THE FLUID SAMPLE IN UPON THE CHIP │──── 408
└─────────────────────────────────────────┘
                    ▼
┌─────────────────────────────────────────┐
│ MEASURE CONDUCTANCE BETWEEN THE WIRES,  │
│ PRODUCING A SAMPLED VALUE OF            │──── 410
│ CONDUCTANCE BETWEEN WIRES IN THE CHIP   │
└─────────────────────────────────────────┘
                    ▼
┌─────────────────────────────────────────┐
│ COMPARE THE SAMPLED VALUE TO THE BASELINE VALUE │──── 412
└─────────────────────────────────────────┘
                    ▼
┌─────────────────────────────────────────┐
│ IF THE SAMPLED VALUE IS DIFFERENT FROM THE BASELINE │
│ VALUE BY MORE THAN A THRESHOLD AMOUNT, PRODUCE AN   │──── 414
│ ALERT THAT THE SUBJECT'S BODY CARRIES THE CORONAVIRUS │
└─────────────────────────────────────────┘
```

FIG. 4

PHYSICAL METHODS FOR LIVING TISSUE INACTIVATION AND DETECTION, AND PHYSICAL METHODS IN USE FOR THE DETECTION AND INACTIVATION OF LIVING BODIES (LIKE EBOLA AND 2019 CORONAVIRUS) IN LIVING SYSTEMS AND NON-LIVING SYSTEMS THEREOF

RELATED APPLICATIONS

This application is a Continuation-in-Part (CIP) of U.S. patent application Ser. No. 17/167,291 filed on Feb. 4, 2021, which claims the benefit of priority under 35 USC § 119(e) of U.S. Provisional Patent Application Nos. 62/970,790 and 62/970,775, both filed on Feb. 6, 2020. The contents of the above applications are all incorporated by reference as if fully set forth herein in their entirety.

FIELD AND BACKGROUND OF THE INVENTION

Pandemic outbreaks of influenza and recently the 2019 coronavirus are increasingly common. There have been many recent outbreaks of influenza virus epidemics, and the t outbreak of the Ebola Virus, cause much concern for world pandemic. In contrast to the regular seasonal epidemics of influenza, these pandemics occur irregularly and can cause high levels of mortality. Influenza pandemics occur when a new strain of the influenza virus is transmitted to human from another animal species. Species that are thought to be important in the emergence of new human strains are pigs, chickens and ducks. The mutation that allows a fast transfer of the swine virus from human to human has already occurred, and it is just a matter of time before the more dangerous avian type H5N1 influenza A will develop such a mutation.

The often occurring outbreaks of the flu virus and currently the 2019 Coronavirus were shown to be hybrid viruses between different types of species: human, swine, horse and avian. Since the lethality rate from avian-human H5N1 is very high (more than 70%) such a mutation (human to human) can be a global threat for humanity. Today there are no rapid and simple kits available that identify people suspected of carrying a new virus. There are two types of technologies available for detection: immunoassay and RT-PCR. With respect to the immunoassay technique, the patient has to develop antibodies for the virus; hence the detection can be made only at a late stage. If antigens are to be detected with prepared antibodies, the disadvantage is that the virus can develop mutations that will be unrecognized by a specific antibody. Since antibody preparation is time and money consuming, it is not practical to develop new kits frequently. RT-PCR on the other hand, is a complicated assay that cannot be performed in a few minutes, and in massive amounts, and false positive rates are high. In addition, mutations are often not detectable by this technique.

There are some enzymatic assays that are under development that can be used for fast detection, however, observing the course of events in the 2009 swine flu outbreak, the time taken to bring a field detection kit to useful application in any given epidemic is too long to be of more than limited use in prevention of spread. The SARS epidemic in 2003, the H5N1 outbreak in 2007, and the swine flu outbreak in 2009 demonstrate this significant drawback. Currently the 2019 coronavirus has exceeded all dreadful predictions. The most common ways for prevention of the spread of the disease were by identifying people with an elevated body temperature, and isolating and quarantining them. However, often healthy people are quarantined with sick people. The Ebola virus causes an acute, serious illness which is often fatal if untreated. Ebola virus disease (EVD) first appeared in 1976 in 2 simultaneous outbreaks, one in Nzara, Sudan, and the other in Yambuku, Democratic Republic of Congo. The latter occurred in a village near the Ebola River, from which the disease takes its name.

2019 Coronavirus causes complications of pneumonia, can be from cytokine storm as a reaction of the body for an unknown pathogen. More than 20000 people have been infected currently and more than 400 people dead.

The 2014 outbreak in West Africa, is the largest and most complex Ebola outbreak since the Ebola virus was first discovered in 1976. There have been more cases and deaths in this outbreak than all others combined. It has also spread between countries starting in Guinea then spreading across land borders to Sierra Leone and Liberia, by air (1 traveler only) to Nigeria, and by land (1 traveler) to Senegal.

It is thought that fruit bats of the Pteropodidae family are natural Ebola virus hosts. Ebola is introduced into the human population through close contact with the blood, secretions, organs or other bodily fluids of infected animals such as chimpanzees, gorillas, fruit bats, monkeys, forest antelope and porcupines found ill or dead or in the rainforest.

Ebola then spreads through human-to-human transmission via direct contact (through broken skin or mucous membranes) with the blood, secretions, organs or other bodily fluids of infected people, and with surfaces and materials (e.g. bedding, clothing) contaminated with these fluids.

Health-care workers have frequently been infected while treating patients with suspected or confirmed EVD. This has occurred through close contact with patients when infection control precautions are not strictly practiced.

It can be difficult to distinguish EVD from other infectious diseases such as malaria, typhoid fever and meningitis. Confirmation that symptoms are caused by Ebola virus infection are made using the following investigations:

antibody-capture enzyme-linked immunosorbent assay (ELISA)
antigen-capture detection tests
serum neutralization test
reverse transcriptase polymerase chain reaction (RT-PCR) assay
electron microscopy
virus isolation by cell culture.

Samples from patients are an extreme biohazard risk; laboratory testing on non-inactivated samples should be conducted under maximum biological containment conditions.

Therefore, there is an urgent need for rapid detection of infectious diseases at main junctions such as airports and public places to prevent the spread of the disease from an outbreak threat to world pandemic, to avoid a large spread of the pathogen, to prevent mixing of pathogens and creation of more dangerous and contagious species of the pathogen. It is also a long felt and unmet need to provide means and methods for early detection and identification of an individual suspected in carrying a pathogen, in order to avoid transferring the pathogen and infecting other people. A prompt and early detection of a disease will allow effective treatment results.

SUMMARY OF THE INVENTION

The invention herein disclosed is designed to meet this long felt need. In particular, a method of identifying the presence of a pathogen in an individual is disclosed. The method comprises steps of (a) making a first recording (R1) of at least one parameter of a body portion of said individual; (b) transmitting a set of impulses characteristic of said pathogen to said body portion; (c) making a second recording (R2) of said specific parameters after said transmitting of said set of impulses; and, (d) determining the difference between R2 relative to R1 wherein said difference is indicative of the presence of said pathogen in said individual.

According to an aspect of some embodiments of the present disclosure there is provided a system for detecting presence of coronavirus in a subject, the system including a first pad for placing a first hand, the pad including a contact to measure conductance of the subject's body, a conductance meter connected to the contact, a second pad for placing a second hand, a source of electromagnetic radiation for irradiating the second pad.

According to some embodiments of the disclosure, the source of electromagnetic radiation includes a source configured to irradiate at frequencies associated with the coronavirus.

According to some embodiments of the disclosure, the system is configured to measure conductance of the subject's body by measuring conductance of the first hand.

According to some embodiments of the disclosure, the system is configured to measure conductance of the subject's body by measuring conductance between the first hand and the second hand.

According to some embodiments of the disclosure, at least one of the first pad and the second pad, are shaped and sized to locate the subject's hand so that the contacts in the pad a located next to a meridians of the subject's hand.

According to an aspect of some embodiments of the present disclosure there is provided a method for detecting presence of coronavirus in a subject, the method including providing a baseline value of conductance of a subject's body, irradiating the subject's body with electromagnetic radiation at frequencies associated with the coronavirus, measuring the conductance of the subject's body, thereby providing a second value of conductance, comparing the second value to the baseline value, and if the second value is different from the baseline value by more than a threshold amount, producing an alert that the subject's body carries the coronavirus.

According to some embodiments of the disclosure, the irradiating includes irradiating at one or more frequencies associated with the coronavirus.

According to some embodiments of the disclosure, the frequencies are selected from a group consisting of 80 KHz, 145.9 KHz, 152.19 KHz, 155 KHz, 165.69 KHz, 291.69 KHz, 304.39 KHz, 350 KHz, 309.89 KHz, 331.39 KHz, 437.6 KHz, 456.5 KHz, 464.89 KHz, 497.1 KHz, 583.5 KHz, 608.7 KHz, 619.89 KHz, 662.7 KHz, 760.89 KHz, 774.79 KHz, 1167 KHz, 1217.5 KHz, 1239.7 KHz, 1312.79 KHz, 1325.5 KHz, 1369.59 KHz, 1394.7 KHz, 1491.2 KHz, 2333.9 KHz, 2435 KHz, 2479.5 KHz, 2651 KHz, 4667.8 KHz, 4870 KHz, 4959 KHz, 5301.89 KHz, 5750 KHz, 9335.6 KHz, 9740 KHz, 9918 KHz, 12930 KHz, 63470 KHz, 182500 KHz, 435290 KHz, 562500 KHz, 793500 KHz, and 995750 KHz.

According to some embodiments of the disclosure, the frequencies are selected from a group consisting of 80 Hz, 145.9 Hz, 152.19 Hz, 155 Hz, 165.69 Hz, 291.69 Hz, 304.39 Hz, 350 Hz, 309.89 Hz, 331.39 Hz, 437.6 Hz, 456.5 Hz, 464.89 Hz, 497.1 Hz, 583.5 Hz, 608.7 Hz, 619.89 Hz, 662.7 Hz, 760.89 Hz, 774.79 Hz, 1167 Hz, 1217.5 Hz, 1239.7 Hz, 1312.79 Hz, 1325.5 Hz, 1369.59 Hz, 1394.7 Hz, 1491.2 Hz, 2333.9 Hz, 2435 Hz, 2479.5 Hz, 2651 Hz, 4667.8 Hz, 4870 Hz, 4959 Hz, 5301.89 Hz, 5750 Hz, 9335.6 Hz, 9740 Hz, 9918 Hz, 12930 Hz, 63470 Hz, 182500 Hz, 435290 Hz, 562500 Hz, 793500 Hz, and 995750 Hz.

According to some embodiments of the disclosure, the irradiating includes irradiating at a plurality of frequencies associated with the coronavirus.

According to some embodiments of the disclosure, the irradiating includes irradiating at the plurality of frequencies simultaneously.

According to some embodiments of the disclosure, the measuring the conductance of the subject's body includes measuring conductance during the irradiating.

According to some embodiments of the disclosure, the measuring the conductance of the subject's body includes measuring conductance after the irradiating.

According to some embodiments of the disclosure, the irradiating includes irradiating one of the subject's hands, and the measuring the conductance of the subject's body includes measuring conductance at the other one of the subject's hands.

According to some embodiments of the disclosure, the irradiating includes irradiating one of the subject's hands, and the measuring the conductance of the subject's body includes measuring conductance at meridians of the subject's hand.

According to some embodiments of the disclosure, the irradiating includes irradiating one of the subject's hands, and the measuring the conductance of the subject's body includes measuring conductance from an irradiated hand to another one of the subject's hands.

According to some embodiments of the disclosure, the irradiating includes irradiating one of the subject's hands, and the measuring the conductance of the subject's body includes measuring conductance from at meridians of the subject's irradiated hand to at meridians of another one of the subject's hands.

According to an aspect of some embodiments of the present disclosure there is provided a system for detecting presence of coronavirus in a subject, the system including a chip with a plurality of wires disposed on or in the chip, a conductance meter arranged to measure conductance between the wires, and biological material associated with the coronavirus disposed on or in the chip.

According to an aspect of some embodiments of the present disclosure there is provided a device for detecting presence of coronavirus in a subject, the system including a chip with a plurality of wires disposed on or in the chip, and biological material associated with the coronavirus disposed on or in the chip.

According to some embodiments of the disclosure, the chip and the biological material are included in a reaction vessel configured to accept a fluid sample taken from a subject.

According to an aspect of some embodiments of the present disclosure there is provided a method for detecting presence of coronavirus in a subject, the method including providing a system as described hereinabove, providing a baseline value of conductance between wires in the chip, providing a fluid sample taken from a subject, disposing the fluid sample in upon the chip, measuring conductance between the wires, producing a sampled value of conductance between wires in the chip, comparing the sampled value to the baseline value, if the sampled value is different from the baseline value by more than a threshold amount, producing an alert that the subject's body carries the coronavirus.

It is thus an object of the invention herein disclosed to provide a method as defined above, wherein said parameters and/or said impulses are electromagnetic frequencies.

It is a further object of this invention to disclose a method as defined above, further comprising steps of detecting the presence or absence of electromagnetic resonance, said electromagnetic resonance is characterized by said difference between R2 and R1, further wherein said presence of said pathogen is correlated with the presence or absence of said electromagnetic resonance.

It is a further object of this invention to disclose a method as defined above, additionally comprising steps of selecting said parameters from a group comprising electromagnetic frequency, conductivity, muscle resistance, electrical resistance, electric current, direct current, surface tension, potential, electromagnetic radiation, wavelength, spectroscopic fingerprint, a transcutaneous electrical nerve stimulation, a Fourier transform infrared spectroscopy (FTIR), a Nuclear magnetic resonance (NMR) or a combination thereof.

It is a further object of this invention to disclose a method as defined above, additionally comprising steps of recording said at least one parameter using a device selected from a group comprising a Zapper, a Bicom, a tensiometer, an SCS-BARS device, a David Tansley transposer, a galvanometer, a Flu master, a Direct Current (DC) resistant meter, a current reading device, a Rife device, an FTIR spectrometer, an NMR spectrometer, MRI device, an imaging device, a tuning fork device or any combination thereof.

It is a further object of this invention to disclose a method as defined above additionally comprising steps of obtaining said set of specific parameters using kinesiology and radiometry methods.

It is a further object of this invention to disclose a method as defined above, additionally comprising steps of determining the difference between R2 relative to R1 wherein said difference is in the range of about 10% to about 25% reduction in R2 relative to R1.

It is a further object of this invention to disclose a method as defined above, additionally comprising steps of identifying the presence of a pathogen selected from a group comprising viruses, bacteria, parasites, fungi, allergens, toxins or a combination thereof.

It is a further object of this invention to disclose a method as defined above, additionally comprising steps of transmitting said set of impulses characteristic to said body portion using a signal generator device.

It is a further object of this invention to disclose a method as defined above, additionally comprising steps of selecting said signal generating device from a group comprising a Zapper, a Bicom, a Flu master, a SCS-BARS device, a David Tansley transposer, a transponder, a transducer, an electromagnetic signal generator, a Rife device, a global diagnostics devise, a tuning fork or a combination thereof.

It is a further object of this invention to disclose a method as defined above, additionally comprising steps of transmitting said set of impulses to said body portion in a contactless manner or without physical contact.

It is a further object of this invention to disclose a method as defined above, additionally comprising steps of transmitting said set of impulses to said body portion in a remote manner.

It is a further object of this invention to disclose a method as defined above, additionally comprising steps of transmitting said set of impulses to said body portion from a substrate.

It is a further object of this invention to disclose a method as defined above, additionally comprising steps of selecting said substrate from a group comprising a pad, a pillow, a patch, a strip, a disk, a medium, a support or a combination thereof.

It is a further object of this invention to disclose a method as defined above, additionally comprising steps of incorporating said pathogen within said substrate.

It is a further object of this invention to disclose a method as defined above, additionally comprising steps of transmitting said set of impulses to say body portion from a substrate preprogrammed with the impulses characteristic to said pathogen.

It is a further object of this invention to disclose a method as defined above, additionally comprising steps of preprogramming said substrate by implementing a software or disc within said substrate, said software or disc contain said impulses characteristic to said pathogen.

It is a further object of this invention to disclose a method as defined above, additionally comprising steps of preprogramming said substrate by a remotely controlled device adapted to produce said impulses characteristic to said pathogen.

It is a further object of this invention to disclose a method as defined above, additionally comprising steps of preprogramming said substrate by a remotely controlled device adapted to produce said impulses characteristic to said pathogen according to a predetermined data base.

It is a further object of this invention to disclose a method as defined above, additionally comprising steps of applying said substrate to said body portion of said individual.

It is a further object of this invention to disclose a method as defined above, additionally comprising steps of selecting said body portion from a group comprising meridian points, acupuncture points, internal part of the palm, foot, neck, reflexology map or atlas, a conventional anatomy map or a combination thereof.

It is a further object of this invention to disclose a method of identifying tumor cells in an individual. The method comprises steps of: (a) making a first recording (R1) of a set of specific parameters of a body portion of said individual; (b) transmitting a set of impulses characteristic of said pathogen to said body portion; (c) making a second recording (R2) of said specific parameters after said transmitting of said set of impulses; and, (d) determining the difference between R2 relative to R1 wherein said difference is indicative of the presence of said tumor cells in said individual.

It is a further object of this invention to disclose a method as defined above additionally comprising steps of identifying tumor cells selected from a group selected from the Rife Index.

It is a further object of this invention to disclose a method of treating tumor cells in an individual. The aforementioned method comprises steps of: (a) making a first recording (R1) of a set of specific parameters of a body portion of said individual; (b) transmitting a set of impulses characteristic of said pathogen to said body portion; (c) making a second recording (R2) of said specific parameters after said transmitting of said set of impulses; and, (d) determining the difference between R2 relative to R1 wherein said difference is indicative of the presence of said tumor cells further wherein said difference causes excitation of said tumor cells sufficient for said cells to stimulate an immunological effect against said tumor cells.

It is a further object of this invention to disclose a system useful for identifying the presence of a pathogen in an individual. The aforesaid system comprises: (a) means for making a first recording (R1) of a set of specific parameters of a body portion of said individual; (b) means for transmitting a set of impulses which correspond to characteristics of said pathogen to said body portion; and, (c) means for making a second recording (R2) of said specific parameters after said transmitting of said set of impulses, wherein the difference between R2 relative to R1 is indicative of the presence of said pathogen.

It is a further object of this invention to disclose a system as defined above, wherein said parameters and/or said impulses are electromagnetic frequencies.

It is a further object of this invention to disclose a system as defined above, wherein said system is adapted to detect the presence or absence of electromagnetic resonance, said electromagnetic resonance is characterized by said difference between R2 and R1, further wherein said presence of said pathogen is correlated with the presence or absence of said electromagnetic resonance.

It is a further object of this invention to disclose a system as defined above, wherein said parameters are selected from a group comprising electromagnetic frequency, conductivity, muscle resistance, electrical resistance, electric current, direct current, surface tension, potential, electromagnetic radiation, wavelength, spectroscopic fingerprint, a transcutaneous electrical nerve stimulation, a Fourier transform infrared spectroscopy (FTIR), a Nuclear magnetic resonance (NMR) or a combination thereof.

It is a further object of this invention to disclose a system as defined above, wherein said means for recording said specific parameters are selected from a group comprising a Zapper, a Bicom, a tensiometer, a SCS-BARS device, a David Tansley transposer, a galvanometer, a Flu master, a Direct Current (DC) resistant meter, a current reading device, an FTIR spectrometer, an NMR spectrometer, MRI device, an imaging device, a global diagnostics devise, a tuning fork device, or a combination thereof.

It is a further object of this invention to disclose a system as defined above, wherein said system is further adapted to obtain said set of specific parameters using kinesiology and radiometry methods.

It is a further object of this invention to disclose a system as defined above, wherein said difference between R2 relative to R1 is in the rage of about 10% to about 25% reduction in R2 relative to R1.

It is a further object of this invention to disclose a system as defined above, wherein said pathogen is selected from a group comprising viruses, bacteria, parasites, fungi, allergens, toxins or a combination thereof.

It is a further object of this invention to disclose a system as defined above, wherein said transmitting means further comprise a signal generating device.

It is a further object of this invention to disclose a system as defined above, wherein said signal generating device is selected from a group comprising a Zapper, a Bicom, a Flu master, a SCS-BARS device, a David Tansley transposer, a transponder, transducer, electromagnetic signal generator, a Rife machine, global diagnostics devise, a tuning fork or a combination thereof.

It is a further object of this invention to disclose a system as defined above, wherein said set of impulses is transmitted to said body portion in a contactless manner or without physical contact.

It is a further object of this invention to disclose a system as defined above, wherein said set of impulses is transmitted to said body portion in a remote manner.

It is a further object of this invention to disclose a system as defined above, wherein said means for transmitting said set of impulses further comprise a substrate adapted to transmit said set of impulses to said body portion.

It is a further object of this invention to disclose a system as defined above, wherein said substrate is selected from a group comprising a pad, a pillow, a patch, a strip, a disk, a medium, a support or a combination thereof.

It is a further object of this invention to disclose a system as defined above, wherein said pathogen is incorporated within said substrate.

It is a further object of this invention to disclose a system as defined above, wherein said substrate is preprogrammed according to said impulses characteristic to said pathogen.

It is a further object of this invention to disclose a system as defined above, wherein said substrate is preprogrammed by software or disc implemented within said substrate, said software or disc contain said impulses characteristic to said pathogen.

It is a further object of this invention to disclose a system as defined above, wherein said substrate is preprogrammed by a remotely controlled device adapted to produce said impulses characteristic to said pathogen.

It is a further object of this invention to disclose a system as defined above, wherein said substrate is preprogrammed by a remotely controlled device adapted to produce said impulses characteristic to said pathogen according to a predetermined data base.

It is a further object of this invention to disclose a system as defined above, wherein said transmitting means further adapted to produce electromagnetic frequencies characteristic of said pathogen.

It is a further object of this invention to disclose a system as defined above, wherein said substrate is applied to said body portion of said individual.

It is a further object of this invention to disclose a system as defined above, wherein said body portion is selected from a group comprising meridian points, acupuncture points, internal part of the palm, foot, neck, reflexology map or atlas, a conventional anatomy map or a combination thereof.

It is a further object of this invention to disclose a system useful for identifying tumor cells in an individual. The system said comprises: (a) means for making a first recording (R1) of a set of specific parameters of a body portion of said individual; (b) means for transmitting a set of impulses characteristic of said pathogen to said body portion; and, (c) means for making a second recording (R2) of said specific parameters after said transmitting of said set of impulses; wherein the difference between R2 relative to R1 is indicative of the presence of said tumor cells in said individual.

It is a further object of this invention to disclose a system as defined above, wherein said tumor cells are selected from a group selected from the Rife Index.

It is a further object of this invention to disclose a system useful for treating tumor cells in an individual. The system comprises: (a) means for making a first recording (R1) of a set of specific parameters of a body portion of said individual; (b) means for transmitting a set of impulses characteristic of said pathogen to said body portion; and, (c) means for making a second recording (R2) of said specific parameters after said transmitting of said set of impulses, wherein the difference between R2 relative to R1 is indicative of the presence of said tumor cells further wherein said difference causes excitation of said tumor cells sufficient for said cells to stimulate an immunological effect against said tumor cells.

It is a further object of this invention to disclose a method for inducing a protective immune response in an individual against a pathogen. The method comprises steps of transmitting a set of impulses characteristic of said pathogen to a body portion, wherein said impulses provokes a cascade reaction sufficient for said pathogen to stimulate an immunological effect against said pathogen.

It is a further object of this invention to disclose a method of early stage prevention of the spread of a contagious disease caused by a pathogen. The method comprises steps of: (a) making a first recording (R1) of at least one parameter of a body portion of said individual; (b) transmitting a set of impulses characteristic of said pathogen to said body portion; (c) making a second recording (R2) of said specific parameters after said transmitting of said set of impulses; (d) determining the difference between R2 relative to R1 wherein said difference is indicative of the presence of said pathogen; and, (e) isolating said individual so as to prevent the spread of said contagious disease.

It is a further object of this invention to disclose a method useful for rapidly screening and identifying the presence of a contagious disease caused by a pathogen. The method comprises steps of: (a) making a first recording (R1) of at least one parameter of a body portion of said individual; (b) transmitting a set of impulses characteristic of said pathogen to said body portion; (c) making a second recording (R2) of said specific parameters after said transmitting of said set of impulses; (d) determining the difference between R2 relative to R1 wherein said difference is indicative of the presence of said pathogen in an individual; and, (e) repeating steps a to do in a plurality of individuals, thereby rapidly screening and identifying the presence of a contagious disease caused by said pathogen.

It is a further object of this invention to disclose a screening system for early detection of a pathogen in an individual. The system comprises: (a) means for making a first recording (R1) of a set of specific parameters of a body portion of said individual; (b) means for transmitting a set of impulses which correspond to characteristics of said pathogen to said body portion; and, (c) means for making a second recording (R2) of said specific parameters after said transmitting of said set of impulses, wherein the difference between R2 relative to R1 is indicative of the presence of said pathogen in said individual.

It is a further object of this invention to disclose a method for creating or updating a data base, said data base comprising at least one parameter characteristic to at least one pathogen. The method comprises steps of: (a) making a first recording (R1) of at least one parameter of a body portion of said individual; (b) transmitting a set of impulses or parameters characteristic of a tested pathogen to said body portion; (c) making a second recording (R2) of said specific parameters after said transmitting of said set of impulses; (d) determining the difference between R2 relative to R1 wherein said difference is indicative of the presence of said tested pathogen in said individual; and, (e) adding said set of impulses or parameters characteristic of said tested pathogen to said data base.

It is a further object of this invention to disclose a method for inducing a cellular response by predetermined activating a molecule in an individual. The method comprises steps of: (a) exposing a body portion of said individual to said activating molecule or to impulses/electron density field/ arrangement characteristic of said activating molecule; and, (b) transmitting a set of impulses characteristic of said molecule to said body portion, wherein said impulses provoke a response or cascade or reaction sufficient for said molecule to stimulate a cellular response.

It is a further object of this invention to disclose a method as defined above, additionally comprising steps of selecting said molecule from a group comprising hormones, transcription factors, enzymes, nucleic acids, proteins or a combination thereof.

It is a further object of this invention to disclose a system as defined above. A method according to claim 55, additionally comprising steps of selecting said cellular response cascade/reaction from a group comprising enzymatic reactions, hormonal reactions, gene translation reactions, cell proliferation, DNA replication, cell death reactions or a combination thereof.

It is a further object of this invention to disclose a method as defined above, additionally comprising steps of selecting said body portion form a group comprising meridian points, acupuncture points, internal part of the palm, foot, neck, reflexology map or atlas, a conventional anatomy map or a combination thereof.

BRIEF DESCRIPTION OF THE SEVERAL VIEWS OF THE DRAWING(S)

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings:

FIG. 2E is a simplified flow chart illustration of a method for detecting presence of coronavirus in a subject according to an example embodiment;

FIG. 4 is a simplified flow chart illustration of a method for detecting presence of coronavirus in a subject according to an example embodiment.

DESCRIPTION OF SPECIFIC EMBODIMENTS OF THE INVENTION

Figure 1:
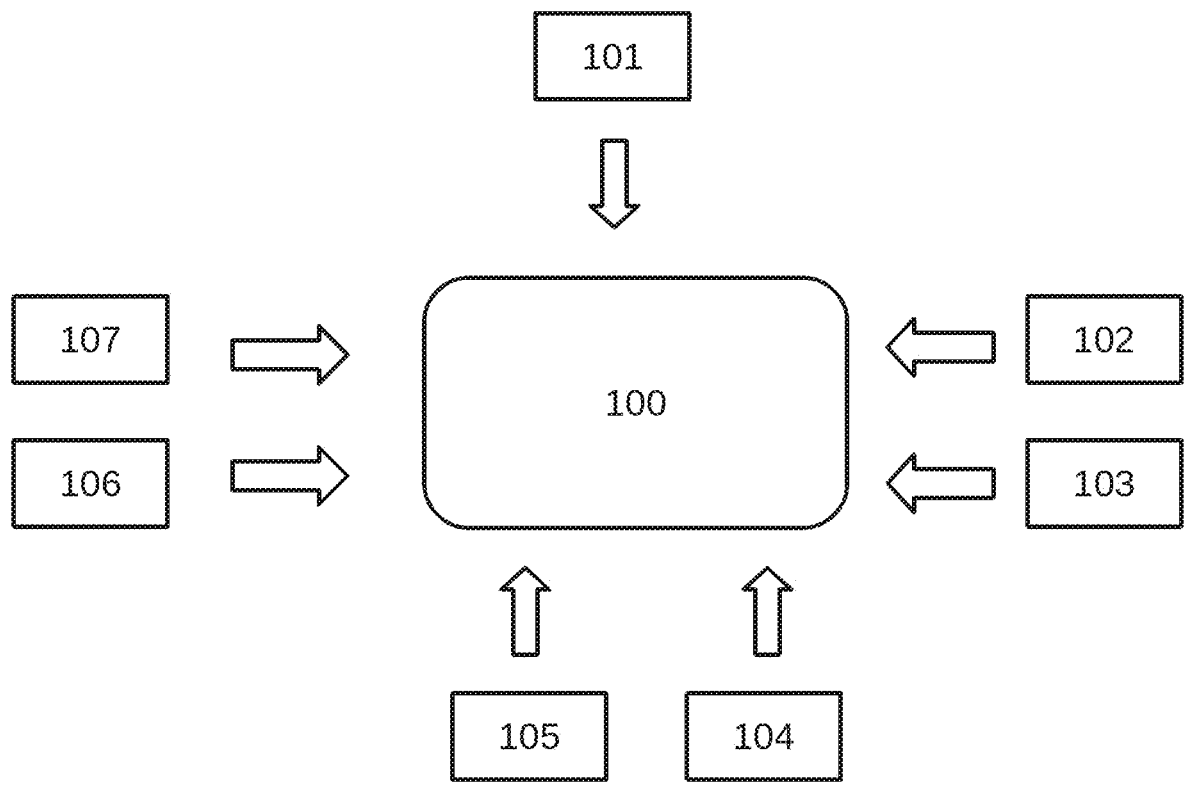
FIG. 1 is an illustration of an example embodiment of the invention.

The present invention provides a method of identifying the presence of a pathogen in an individual. The aforementioned method comprising steps of: (a) making a first recording (R1) of at least one parameter of a body portion of said individual; (b) transmitting a set of impulses characteristic of said pathogen to said body portion; (c) making a second recording (R2) of said specific parameters after said transmitting of said set of impulses; and, (d) determining the difference between R2 relative to R1 wherein said difference is indicative of the presence of said pathogen in said individual.

In accordance with a main aspect of the invention, the detailed above method further comprises steps of detecting the presence or absence of electromagnetic resonance. The electromagnetic resonance is characterized by the difference between R2 and R1. In accordance with a further main aspect of the invention, the presence of the pathogen is correlated with the presence or absence of the electromagnetic resonance.

It is within the scope of the invention to provide a rapid method for detection of a virus, by measuring the difference of the electric current of the body, in several acupuncture points, or selected points in the body after externally applying the virus to the body portion. More specifically, a sample containing a specific virus, energy pattern characteristic of the virus, or finger print frequency pattern of the virus is applied to the tested individual. If the person has in his body the specific virus that was externally applied to him, the two sources of similar or identical viruses are creating interference, or they resonate, and as a result, there is a change in the electromagnetic field of the tested person.

According to one aspect of the invention, the electromagnetic field in acupuncture points of the tested individual declines when the body of the tested person is infected with the same virus that was applied to him externally. If the person is not infected with the same virus, then, after externally applying the sample with virus to the tested person, the electromagnetic field in acupuncture points remains the same as the control level.

According to further aspects of the invention, the tested person can be provided with two sources of the same virus, applied externally to two different points in his body. If the person is not infected with the virus, the second source of virus would change the electric or electromagnetic field in the body, reducing or raising the level of the control electromagnetic measurement.

In accordance with a further embodiment of the invention, the aforementioned method additionally comprising steps of selecting the parameters from a group comprising electromagnetic frequency, conductivity, muscle resistance, electrical resistance, electric current, direct current, surface tension, potential, electromagnetic radiation, wavelength, spectroscopic fingerprint, Transcutaneous electrical nerve stimulation (TENS), a Fourier transform infrared spectroscopy (FTIR), a Nuclear magnetic resonance (NMR) or a combination thereof.

In accordance with a further embodiment of the invention, the aforementioned method additionally comprises steps of identifying the presence of a pathogen selected from a group comprising viruses, bacteria, parasites, fungi, toxins, allergens or a combination thereof.

Thus according to one aspect of the method of the present invention a set of parameters is recorded from a body portion. The first recording measures the basal or reference level of the body portion. The second recording is performed after applying a set of impulses characteristic to a pathogen. A difference between the first and the second readings of the body portion is indicative of the presence of electromagnetic resonance or interference produced by the externally introduced pathogen. The electromagnetic resonance is thus correlated to the presence of an identical pathogen in the body portion.

According to a preferred embodiment of the invention the measuring and recording of the first and second readings is performed by a current or an electromagnetic measuring device, that is adapted to recognize the change in polarization of the electromagnetic field of the body that is interrupted by the externally introduced pathogen energy resonance. The change in polarization is adapted to show the difference in the electric or electromagnetic field due to the external introduction of a pathogen electromagnetic frequency fingerprint pattern to the person being examined.

The recording and/or measuring means may include devices such as a Direct Current (DC) current resistant meter, a galvanometer, Zapper, Bicom, tensiometer, a SCS-BARS device, David Tansley transposer, flu master, a current reading device, a Rife device, an FTIR spectrometer, an NMR spectrometer, MRI device, an imaging devise, a global diagnostics devise, a tuning fork device or a combination thereof.

According to a further embodiment of the invention, the presence or absence of a change in polarization of the electromagnetic field is positively correlated with the presence or absence of an electromagnetic resonance caused by interference of externally introduced electromagnetic frequencies with the electromagnetic frequencies of a body portion. The aforesaid resonance is indicative of the presence of the same pathogen as externally introduced in said body portion of an individual.

According to preferred embodiments of the present invention the largest difference between a control measure and a positive result indicates the existence of a specific examined pathogen. The measurement or test is by (but not limited to) making a first and second recording of parameters in the inner part of the palm and more specifically to the tissue connecting the inner part of the palm and the hand. It is within the scope of the present invention that the experiments performed in this specific body portion showed a large difference between the first (R1) and second (R2) recordings (see Tables 1-3 below).

According to a further aspect of the invention, a set of impulses or signals characteristic to a specific pathogen or several pathogens is transmitted to the body portion.

According to one embodiment of the invention, the aforementioned body portion is selected from a group comprising meridian points, acupuncture points, internal part of the palm, foot, neck, reflexology map or atlas, a conventional anatomy map or a combination thereof.

According to a further embodiment of the invention, the aforementioned set of impulses is transmitted to said body portion in a contactless manner or without physical contact.

According to a further embodiment of the invention the set of impulses is transmitted to the body portion in a remote manner.

According to another embodiment, the set of impulses characteristic to the tested pathogen are transmitted to the body portion from a signal generator device. The term 'signal generator device' used herein refers in a non-limiting manner to a Zapper, a Bicom, a Flu master, a SCS-BARS device, a David Tansley transposer, a transponder, transducer, electromagnetic signal generator, a Transcutaneous electrical nerve stimulation (TENS) device, a Rife devise, a global diagnostics devise, a tuning fork or a combination thereof.

According to a further embodiment of the present invention, the set of impulses or signals may be transmitted to the body portion from a substrate.

As used herein the term 'substrate' refers in a limiting manner to a medium, a moiety, a support, a pad, a pillow, a patch, a strip, a surface, a disk or a combination thereof.

According to a further embodiment of the invention, the aforementioned substrate may contain the intrinsic electromagnetic frequencies that are characteristic of a pathogen. The aforementioned electromagnetic frequencies are transmitted to the body portion.

According to a further embodiment of the invention, the aforementioned substrate may contain the tested pathogen or a plurality of tested pathogens.

According to a further embodiment of the invention, the aforesaid substrate may be preprogrammed with the impulses characteristic to the tested pathogen or pathogens.

According to a further embodiment of the invention, the aforesaid substrate is preprogrammed by software or disc implemented within the substrate. The software or disc contains the impulses characteristic to the pathogen.

According to a further embodiment of the invention, the aforesaid substrate is preprogrammed by a remotely controlled device. Such a device may be a signal generator device, for example a zapper device, or a "Rife machine" which produces signals and pulses characteristic to specific pathogens according to a predetermined data base.

According to a further embodiment such a data base that can be used by the method of the present invention is, but not limited to the Rife index. The Rife index lists frequencies of about 52 viruses, including typhoid, tuberculosis, and cancer.

Dr. Royal Rife theorized that every virus, bacterium, parasite and other pathogen is particularly sensitive to a specific frequency and can be destroyed by intensifying that frequency until it explodes. Rife claimed that he could find a Mortal Oscillatory Rate (MOR) for various pathogenic organisms. Rife claimed to have documented the precise frequencies which destroyed specific organisms.

In accordance with the present invention, the Rife Machine equipment is an instrument that generates specific user-inputted frequencies and harmonics based on Rife's observations that intensifying the resonant frequency of a specific virus or bacteria destroys it. These frequencies and harmonics are transmitted to the body via hand-held, footplate, or stick-on electrodes.

The rife machine is based upon the theory that every molecule vibrates, or oscillates, at its own unique frequency and resonates with that frequency.

The present invention discloses a very rapid method for detection of a pathogen in an individual. The aforementioned method may include measuring the change in the polarity of the body electric current, in several acupuncture points, and other points in the body. In the test, a sample containing a specific pathogen, energy pattern of the pathogen, or finger print frequency pattern of the pathogen is applied to the tested person. If the person has in his body the specific pathogen that was applied to him externally, the two sources of similar or identical pathogens are creating interference, or they resonate, and as a result, there is a change in the electrical field of the tested person.

One explanation for the observed physical phenomenon is that the electric field in acupuncture points of the body drops when the body of the tested person is infected with the same pathogen that was applied to him externally. If the person is not infected with the same pathogen as applied to him externally, then, the electrical field in the acupuncture points remains the same as the control level.

This test may be applied in many different ways, as exemplified in the present invention. In accordance with certain embodiments of the invention, the provided method may be applied to pathogens, including viruses as anthrax and influenza, bacteria, parasites fungi and allergens. As a positive control, the tested person may be applied with two sources of the same pathogen, positioned on two different places externally on his body. If the person is not infected with the pathogen, the second source of the pathogen would change the electric field in the body, reducing or raising the control level of the electric measurement.

Without wishing to be bound by theory, the following definitions, explanations and theories are provided herewith in accordance with aspects of the present invention:

As used herein the term 'resonance' refers to the tendency of a system to oscillate with larger amplitude at some frequencies relative to other frequencies. These are known as the system's resonant frequencies, or resonance frequencies. At these frequencies, even small periodic driving forces can produce large amplitude oscillations. Electrical resonance occurs in an electric circuit at a particular resonance frequency when the impedance between the input and output of the circuit is at a minimum, or when the transfer function is at a maximum. More specifically this occurs when the impedance between the input and output of the circuit is almost zero and when the transfer function is close to one.

The term 'interference' used herein refers to the addition or superposition of two or more waves that result in a new wave pattern. Interference usually refers to the interaction of waves that are correlated or coherent with each other, either because they originate from the same source or because they have the same or nearly the same frequency. If two of the components or waves are of the same frequency and phase the wave amplitudes are reinforced, producing constructive interference. Whereas, if the two waves are out of phase the result is destructive interference, producing smaller peaks than each of the waves alone or complete annulment if they are of equal amplitude.

The term 'electromagnetic interference' used herein refers to a disturbance that affects an electrical circuit due to either electromagnetic conduction or electromagnetic radiation emitted from an external source. The disturbance may interrupt, obstruct, or otherwise degrade or limit the effective performance of the circuit. The source may be any object, artificial or natural, that carries rapidly changing electrical currents.

Reference is now made to a tuning fork, which may herein refer to an acoustic resonator in the form of a two-pronged fork with the prongs (tines) formed from a U-shaped bar of elastic metal (usually steel). It resonates at a specific constant pitch. The pitch that a particular tuning fork generates depends on the length of the two prongs. In accordance with some embodiments of the invention, such a tuning fork plays a role in several alternative medicine modalities, such as sonopuncture and polarity therapy.

It is well established in the spectroscopy field is that every object has a fingerprint frequency. According to molecular mechanics theories, the total energy of a molecule, which is proportional to a specific wave length, is determined by the sum of energies which includes all the energy components, the kinetic energies and potential energies of a single bond and/or interactions within a molecule. The energy components include bond vibration, rotation, bending, electrostatic energy etc. The Schlesinger equation in quantum mechanics, for example describes energy and wavelength descriptors. Thus, without wishing to be bound by theory, the structure of a certain molecule or object is directly proportional to the exact wavelength that it produces. Similarly, in Infrared (IR) spectroscopy, which refers to the infrared region of the electromagnetic spectrum, each molecule has a specific fingerprint which is characteristic to the molecule.

Reference is now made to the Nuclear magnetic resonance (NMR) technique that may be used by the method of the present invention. In NMR the structure of a molecule can be identified based on a minute change in its magnetic field. Nuclear magnetic resonance (NMR) is a property of a magnetic nuclei exposed to a magnetic field and applied electromagnetic (EM) pulse or pulses, which cause the nuclei to absorb energy from the EM pulse and radiate this energy back out. The energy radiated back out is at a specific resonance frequency which depends on the strength of the magnetic field and other factors. This allows the observation of specific quantum mechanical magnetic properties of an atomic nucleus. All nucleons have the intrinsic quantum property of spin. It is the magnetic moment that allows the observation of NMR absorption spectra caused by transitions between nuclear spin levels. Electron spin resonance (ESR) is a related technique which detects transitions between electron spin levels instead of nuclear ones. NMR allowed a very accurate determination of the structure of molecules (proteins) that have 30000 or more atoms. In such molecules, every hydrogen can be identified.

Reference is now made to the Fourier transform infrared spectroscopy (FTIR) technique that may be used to obtain an infrared spectrum of absorption, emission, photoconductivity or Raman scattering of a solid, liquid or gas. An FTIR spectrometer simultaneously collects spectral data in a wide spectral range. The FTIR technique confers a significant advantage over a dispersive spectrometer which measures intensity over a narrow range of wavelengths at a time.

Reference is now made to the Magnetic resonance imaging (MRI), or nuclear magnetic resonance imaging (NMRI) technique that may be used by the method of the present invention. MRI uses a powerful magnetic field to align the nuclear magnetization of hydrogen atoms in water in the body. Radio frequency (RF) fields are used to systematically alter the alignment of this magnetization. This causes the hydrogen nuclei to produce a rotating magnetic field detectable by the scanner. This signal can be manipulated by additional magnetic fields to build up enough information to construct an image of the body. Thus the MRI technology is based upon the principle of identifying water molecules in the body, by the change of their neighboring environment.

Reference is now made to the water cluster and the molecules' shared electron-density theories. In accordance with these theories which support the present invention yet without wishing to be bound by theory, it is acknowledged that the water clusters imitate molecular structures. The following is an optional explanation for the above theory. Water molecules have the property of gathering in clusters, and imitating molecular structure. The common feature between an imitating water cluster molecule, and the molecule itself, is their identical electron-density. This was confirmed in many crystal structures, for example, in the crystal structure of Avidin-Biotin, in which, instead of the Biotin molecule within the Avidin structure, there are five water molecules exhibiting electron-density which is identical to the Biotin. These water molecules imitate its three dimensional structure (Meir Wilzeck). Thus the electron-density is identical between a particular molecule and the water clusters that are ordered in its three-dimensional space.

According to other aspects of the invention, a function of a magnetic or an electromagnetic field could be expressed as the sum of the perpendicular vectors in any point of the electron-density spatial dispersement. Thus, the electron-density induces a specific magnetic or electromagnetic field with particular direction and intensity. The progression of the magnetic or electromagnetic field constantly forms a set of clusters.

The clusters are formed in the microenvironment of the field progression, vertically to the electromagnetic wave direction. This correspondence between the formed wave and the clusters acts as a potential manifestation mechanism, where one predates or predicates the other, yet both are interdependent of each other. The cluster and the wave provide a dual disturbance system of information and manifestation. Whereas the wave or field provides informational functionality, the cluster is the constantly formed disturbance.

Without wishing to be bound by theory, it is acknowledged that the clusters function as a projection of the electromagnetic wave function in one dimension, translating the magnetic or electromagnetic field polarity into structure and form which has time, space and direction.

In accordance with a further aspect of the water cluster theory supporting the invention, it is well known that a human body contains about 60-70% of water. The target action of a hormone molecule that is formed in the brain gland is in a remote organ. It is highly surprising that although the amount of hormone produced by a gland is very small, specifically, less than 10-12 pmol, the information directed to the remote organ is transferred very rapidly, almost immediately. Without wishing to be bound by theory, it is assumed that the hormone molecule, when produced, is secreted from the gland, and the information is transmitted, in the form of a water cluster that mimics the hormone molecule. The aforementioned information can be transferred by a wave of the same cluster forming hydrogen bonds, in the specific molecular frequency, to the desired organ. The water cluster reacts with the surface of the protein, and provides feedback information to the brain. Thus, proteins are reacting with specific water clusters, which can either activate their enzymatic or receptor activities or adversely, repress their activity when reacting with other water clusters.

In accordance with the above described water cluster theory, it is noted that the pH of water is affected by the formation of water clusters, and water cluster waves. The pH, defined by $-\log [H^+]$, is adversely represents the concentration of protons in water solutions. In a neutral pH there are certain amounts of free protons. When water molecules are clustered together, a form initiation or a certain energy frequency occurs, which is in the energy range of hydrogen bond formation (5-7 kcal/mol), then, the concentration of $[H^+]$ decreases, and the pH of the system increases.

When electroencephalogram (EEG) waves recorded from a person, in the energy range of 5-7 kcal/mol, are radiated on water or another person, the electrical energy frequencies affects the water quality of the person, or vessel content, by lowering or elevating their pH, and initiating a hydrogen bond wave field that may affect the body proteins. The resulted effect on the body proteins is specific to the water cluster wave which can up regulate or down regulate the protein activity according to its molecular effect on each protein. The creation of positive wave fields often results in the formation of high level ordered water that elevates the pH, and generally improves the micro environment around the proteins, allowing them to interact better within themselves, and produce signals more efficiently, as well as to improve the reaction rates.

Thus, in accordance with main aspects of the invention, any pathogen has several frequencies, different wave shapes, electromagnetic, elliptic etc. The frequency can be recorded by an external source, and its interaction with the body frequencies can be measured and recorded.

In accordance with a further embodiment of the present invention the aforementioned frequencies can be recorded by external sources and devices such as the zapper device.

Reference is now made to the signal generator devices that may be used in the present invention. According to embodiments of the present invention, a signal generator device is a device which is adapted to produce preprogrammed electromagnetic frequencies. Such signal generator devices may include in a non-limiting manner zappers, Bicom, David Tansley transposer, Clark zapper and a Rife device.

Such equipment is known in the art for producing pathogen and other objects electromagnetic frequencies. According to one embodiment of the invention the pathogen or virus electromagnetic frequencies or signals are obtained from biological material from the Center for Disease Control and prevention (CDC). According to another embodiment of the invention, data collected from individual people is used to build a data base to alert on newly mutated viruses or pathogens and to detect them in real time in different places in the world.

Special designed equipment and apparatus, built to generate resonant frequencies and wave shapes intended to eliminate parasites, bacteria, fungi or viruses and also to charge with energy the glands and organs of the body, are known in the art.

Some of these apparatuses are able to automatically screen through selected frequency limits through the body and to display the list of parasites, bacteria, fungi and viruses found in the body. Other devices are known, that are designed and built to individually generate the amplitude and frequency that destroy the selected parasite, fungus or virus. Subsequent scans or sweeps determine if said parasite/bacteria/fungus/virus is still present or was eliminated, and this procedure can be applied to each component of a detection list. Other simpler equipment's are also known, such as the ZAPPER that generates square signals having a frequency between 2,000 and 40,000 Hz. According some embodiments, a period of application of about 7 minutes, is followed by a 20 minutes pause, and this cycle being repeated three times. Common manufactured equipment's are designed following the researches published by Dr. Hulda Clark (the 'Cure of All Diseases") herein referred to as Clark zapper or zapper.

According to a further embodiment of the invention the impulses, signals or electromagnetic frequencies are characteristic to a specific pathogen or a collection of pathogens.

Reference is now made to a Transcutaneous electrical nerve stimulation (TENS or TeNS), that may be used by the method of the present invention, which is an electrical stimulation produced by a portable stimulator and used to treat pain. TENS may covers the complete range of transcutaneous applied currents used for nerve excitation although the term is often used with a more restrictive intent, namely to describe the kind of pulses produced by portable stimulators used to treat pain. The unit is usually connected to the skin using two or more electrodes. Generally TENS is applied at high frequency (>50 Hz) with an intensity below motor contraction (sensory intensity) or low frequency (<10 Hz) with an intensity that produces motor contraction.

The suggested method and system may be applied in airports and public places without limitation.

Reference is now made to an example of an examination test performed according to the method of the present invention. A first reading (R1) of the electromagnetic frequency of, for example, the 5 meridians of the hand is taken in zero point. Then, a predetermined external pathogen is introduced to the tested individual. The pathogen can be introduced as a patch containing the pathogen or a preprogrammed patch containing the electromagnetic frequencies characteristic to the pathogen, or the pathogen is introduced in the meridians, or by transmitting impulses characteristic to the pathogen, for example by a signal generator device known in the art. A second reading (R2) is taken in order to determine the change in the electromagnetic frequencies in the meridian points after exposure to the external pathogen. The second reading R2 expresses the change in the electrical current of the tested tissue. Such readings can also be performed using non equipment methods as known in kinesiology and radiometric methods.

According to one embodiment of the invention, the difference between R2 and R1 is preferably in the range of between about 10% to about 25% reduction in R2 relative to R1, when the external pathogen is introduced, or if the person is infected with a similar pathogen. If the person is not infected with any of the pathogens introduced externally, the second reading is similar to the first reading, at least at half of the tested points in the body. The validity of the test is evaluated by applying a further recording measure (R3) with the same pathogen. A patch containing the same pathogen or a preprogrammed patch containing electromagnetic frequencies characteristic to the same pathogen, is externally introduced to a different location in the body of the same individual. If the first electromagnetic frequency resonates or interferes with the frequencies transmitted by the pathogen (R3), there is a resonance that infers with the electric field, and creates a change in the polarization.

The present invention further provides a system for identifying the presence of a pathogen in an individual. The system comprising: (a) means for making a first recording (R1) of a set of specific parameters of a body portion of the individual; (b) means for transmitting a set of impulses which correspond to characteristics of the pathogen to the body portion; and (c) means for making a second recording (R2) of the specific parameters after the transmitting of the set of impulses, wherein the difference between R2 relative to R1 is indicative of the presence of the pathogen in the individual.

It is emphasized that the present invention further provides a method and system for identifying and treating tumor cells in an individual.

According to one aspect, the present invention provides a method of identifying tumor cells in an individual. The method comprising steps of: (a) making a first recording (R1) of a set of specific parameters of a body portion of the individual; (b) transmitting a set of impulses characteristic of the pathogen to the body portion; (c) making a second recording (R2) of the specific parameters after the transmitting of the set of impulses; and, (d) determining the difference between R2 relative to R1 wherein the difference is indicative of the presence of the tumor cells.

The tumor cells may be selected from a group selected from the Rife Index.

According to a further aspect, the present invention provides a method of treating tumor cells in an individual. The method comprising steps of: (a) making a first recording (R1) of a set of specific parameters of a body portion of the individual; (b) transmitting a set of impulses characteristic of the pathogen to the body portion; (c) making a second recording (R2) of the specific parameters after the transmitting of the set of impulses; and, (d) determining the difference between R2 relative to R1 wherein the difference is indicative of the presence of the tumor cells further wherein the difference causes excitation of the tumor cells sufficient for the cells to stimulate an immunological effect against the tumor cells.

The present invention further provides a system useful for identifying tumor cells in an individual. The system comprising: (a) means for making a first recording (R1) of a set of specific parameters of a body portion of the individual; (b)

means for transmitting a set of impulses characteristic of the pathogen to the body portion; and, (c) means for making a second recording (R2) of the specific parameters after the transmitting of the set of impulses; wherein the difference between R2 relative to R1 is indicative of the presence of the tumor cells.

The present invention further provides a system useful for treating tumor cells in an individual. The system comprising: (a) means for making a first recording (R1) of a set of specific parameters of a body portion of the individual; (b) means for transmitting a set of impulses characteristic of the pathogen to the body portion; and, (c) means for making a second recording (R2) of the specific parameters after the transmitting of the set of impulses, wherein the difference between R2 relative to R1 is indicative of the presence of the tumor cells further wherein the difference causes excitation of the tumor cells sufficient for the cells to stimulate an immunological effect against the tumor cells.

The present invention further provides means and method for inducing a protective immune response against a pathogen in an individual.

Reference is now made to a method for inducing a protective immune response against a pathogen in an individual. The method comprises steps of transmitting a set of impulses, characteristic of the pathogen, to a body portion. It is herein emphasized that the impulses provoke a cascade reaction sufficient for the pathogen to stimulate an immunological effect against the pathogen.

Reference is now made to a method of early stage prevention of the spread of a contagious disease caused by a pathogen. The method comprising steps of: (a) making a first recording (R1) of at least one parameter of a body portion of the individual; (b) transmitting a set of impulses characteristic of the pathogen to the body portion; (c) making a second recording (R2) of the specific parameters after the transmitting of the set of impulses; (d) determining the difference between R2 relative to R1 wherein the difference is indicative of the presence of the pathogen; and, (e) isolating the individual so as to prevent the spread of the contagious disease.

Reference is now made to a method useful for rapidly screening and identifying the presence of a contagious disease caused by a pathogen. The aforementioned method comprising steps of: (a) making a first recording (R1) of at least one parameter of a body portion of the individual; (b) transmitting a set of impulses characteristic of the pathogen to the body portion; (c) making a second recording (R2) of the specific parameters after the transmitting of the set of impulses; (d) determining the difference between R2 relative to R1 wherein the difference is indicative of the presence of the pathogen in an individual; and, (e) repeating steps a to do in a plurality of individuals, thereby rapidly screening and identifying the presence of a contagious disease caused by the pathogen.

Reference is now made to a screening system for early detection of a pathogen in an individual. The system comprising: (a) means for making a first recording (R1) of a set of specific parameters of a body portion of the individual; (b) means for transmitting a set of impulses which correspond to characteristics of the pathogen to the body portion; and, (c) means for making a second recording (R2) of the specific parameters after the transmitting of the set of impulses, wherein the difference between R2 relative to R1 is indicative of the presence of the pathogen in the individual.

Reference is now made to a method for creating or updating a data base, the data base comprising at least one parameter characteristic to at least one pathogen. The aforesaid method comprising steps of: (a) making a first recording (R1) of at least one parameter of a body portion of the individual; (b) transmitting a set of impulses or parameters characteristic of a tested pathogen to the body portion; (c) making a second recording (R2) of the specific parameters after the transmitting of the set of impulses; (d) determining the difference between R2 relative to R1 wherein the difference is indicative of the presence of the tested pathogen in the individual; and, (e) adding the set of impulses or parameters characteristic of the tested pathogen to the data base.

Reference is now made to a method for inducing a cellular response by predetermined activating a molecule in an individual. The method comprising steps of: (a) exposing a body portion of the individual to the activating molecule or to impulses/electron density field/arrangement characteristic of the activating molecule; and, (b) transmitting a set of impulses characteristic of the molecule to the body portion, wherein the impulses provoke a response or cascade or reaction sufficient for the molecule to stimulate a cellular response.

According to one embodiment, the method for inducing a cellular response as detailed above, additionally comprising steps of selecting the molecule from a group comprising hormones, transcription factors, enzymes, nucleic acids, proteins or a combination thereof.

According to a further embodiment, the method for inducing a cellular response as detailed above, additionally comprising steps of selecting the cellular response cascade/reaction from a group comprising enzymatic reactions, hormonal reactions, gene translation reactions, cell proliferation, DNA replication, cell death reactions or a combination thereof.

According to a further embodiment, the method for inducing a cellular response as detailed above, additionally comprising steps of selecting the body portion form a group comprising meridian points, acupuncture points, internal part of the palm, foot, neck, reflexology map or atlas, a conventional anatomy map or a combination thereof.

The following examples are presented in order to more fully illustrate certain embodiments of the invention. They should in no way, however, be construed as limiting the broad scope of the invention. One skilled in the art can readily devise many variations and modifications of the principles disclosed herein without departing from the spirit and scope of the invention.

Example 1

The aim of the experiment described below is to examine effect of two different sources of Flu electromagnetic Frequency Fingerprint (FFF) that are placed externally to the body on a person that have the flu, relative to a person that does have the flu. The two sources of flu used in the experiment are the following:

1. Flu master, prepared by Larry steel from Steel health center. The flu master may be a rubber disk loaded with electromagnetic frequency fingerprint characteristic of various influenza viruses that exist in the data base of the David Tansley transposer equipment. This equipment is equivalent to the equipment available by Hulda Clack Zapper.

2. Human H1N1; a vial with H1N1 virus titer derived from a tissue culture. The energy of the H1N1 virus prepared by putting a flask with 66% kabbalah water and 33% ethanol, for 24 hours adjacent to a flask containing the virus, at 4° C.

Three people were exposed to the same treatments applied in the following order:

a. Control—measuring the control electromagnetic field of an individual in the acupuncture points of the palm, in five main points along the internal part of the palm.

b. Flu master—applying the flu master to the same individual, at the same points in the body as described above, and measuring the resistance reaction due to the exposure to the flu master using his second hand.

c. H1N1 virus—applying a human H1N1 virus, either live or the electromagnetic frequency fingerprint (FFF) characteristic to the virus, to the same individual, at the back of the individual's neck, or any point chosen (must be constant for the three tested individuals during the measurement) and measuring the resistance as before in b.

The measuring device used in this exemplified experiment is a galvanometer for DC current. The results of the experiment in three independent individuals can be observed in Tables 1, 2 and 3. It is noted the meridian measurement, is the junction between the palm and the hand, and it is found in all cases to show the most significant difference between the initial control reading and the measurement after exposure to the virus, and therefore it is chosen as the acupuncture point of choice (APC).

TABLE 1

The measured electromagnetic frequency of individual-1 before and after externally applying a flu virus source.

| Measurement number (meridian measurements) | Control | Flu master | H1N1 Source |
|---|---|---|---|
| 1 | 47 | 73 | 50 |
| 2 | 49 | 71 | 47 |
| 3 | 60 | 75 | 47 |
| 4 | 59 | 73 | 45 |
| 5 | 50 | 70 | 44 |

TABLE 2

The measured electromagnetic frequency of individual-2 before and after externally applying different sources of flu virus.

| Measurement number (meridian measurements) | Control | Flu master | H1N1 (Source 1) | H1N1 (Source 2) |
|---|---|---|---|---|
| 1 | 50 | 75 | 63 | 55 |
| 2 | 47 | 65 | 52 | 57 |
| 3 | 53 | 65 | 58 | 55 |
| 4 | 54 | 60 | 65 | 55 |
| 5 | 45 | 62 | 55 | 55 |

TABLE 3

The measured electromagnetic frequency of individual-3 after externally applying a flu virus source.

| Measurement number (meridian measurements) | Control | H1N1 source |
|---|---|---|
| 1 | 52 | 55 |
| 2 | 60 | 57 |
| 3 | 70 | 55 |
| 4 | 60 | 55 |
| 5 | 60 | 55 |

The above described results show the effectively of the herein disclosed method for identifying the presence of a pathogen in an individual. By externally applying to a body portion a pathogen or a source of the same pathogen, having the electromagnetic field characteristic of the pathogen, a difference in the electromagnetic measure can be observed if person is infected or artificially introduced with the same pathogen (Tables 1 and 2). If the pathogen is absent in the individuals body, the measured electromagnetic current remains the same as the control level (Table 3).

Example 2

Use of the Method of the Present Invention for Screening Passengers Having Contaminating Disease in Airports:

The method of the present invention can be used to screen passengers, for example in the airport for having a contaminating disease and prevent the spread of the disease before it becomes a pandemic. A typical test which may be applied in airports may be the following: A passenger is asked to put his left palm on a surface, connected to a reading device and his control measure is being read. Then, he is asked to put his second palm on a second surface that contains an electromagnetic frequency fingerprint characteristic to a certain pathogen, and a second measure is being read. If the second reading is significantly different from the control, the passenger is suspected to be contaminated with the same pathogen as introduced to him externally. In this case the passenger is asked to pass the same procedure with a second pathogen probe. If the reading is similar to the control the passenger is allowed to continue with the boarding. Thus in this first screening a yes or no result is obtained within seconds.

People, who are found positive in the first screening test, undergo a second, more accurate test. This test can be, for example PCR and immunoassay techniques that are used to determine more accurately the condition and level of the pathogen in the body, the virulence level, and the origin of the pathogen (for example, bird swine or human).

Example 3

Creating Electromagnetic Frequency Patches for Single Use:

The impulses or electromagnetic frequency characteristic to a pathogen, which are generated by a signal generator device such as a zapper or recorded in a computer, are transmitted into energy patches that hold the energy. An isolation form, rubber or any other isolation known in the art is used to maintain the electromagnetic frequencies active. The frequency patches can be used for diagnosis, as a single use device, to prevent contamination, or can be used for treatment. In the case of pandemics the patches can be used for prevention and building up resistance, as well as for initial treatment.

The method of the present invention can be applied not only for virus diagnosis, but as a long term use for treatment (see Hulda Clark Zapper). The means and method of the present invention can be used for anti-viral, anti-bacterial, anti-parasites, anti-toxins and anti-allergens, as long as treatment for cancer.

Example 4

Detection of Ebola Virus or 2019 Coronavirus or any Virus Through a Smartphone Application.

The sensitive conduct meter KT-10 S/C includes an App to display real time scanner profiles on Android operated smart phones and tablets. Real time animated graphical outputs are displayed on the smart phone's screen while scanning. The application can also be used as a KT-10 S/C memory data browser to display field measurements/records, allowing the user to pan and zoom on the scanner graph.

Additional text notes can be added to the current or previously stored data with an Android smart phone or tablet. Thus, for a home s diagnostics test or a test in the airport, the person to be tested will place his finger on his touch screen in the smartphone app. The smartphone contains a conductivity measurement unit as KT-10 S/C, The smartphone is connected via the web to a frequency database center. Once the initial conductivity measurement is taken, a pulse that contains Ebola frequencies is submitted, the conductivity is taken again (it can also be done simultaneously, by letting the instrument take a zero point, and then submitting the frequencies and taking the test reading). A set of frequencies as follows provides an example for the frequencies typical for Ebola: (taken from common knowledge from the internet) are: 0.03, 0.12, 0.95, 2.50, 22.50, 51.33, 193.50, 356.72, 426.16, 567.70 http://altered-states(dot)net/barry/newsletter135/frequencies(dot)html/.

Exact set of frequencies will be scanned directly from the plane. The result can be reported directly by the database center as a security check for getting on the plane. This type of method answers a serious concern in the frequencies screening test, which is the danger of infectivity from one person to another. If the test will be done in one central place, the probes for conductivity should be for one time use, and replaced from one person to another.

Example 5

Activation of Glutathione Synthase Activity in the Body, Using Electromagnetic Patches Attached at Meridian Points.

A patch that contain the molecule glutathione, or a combination of amino acids that mimic or correspond in a specified manner to glutathione, or impulses or electromagnetic frequencies characteristic to the molecule as read from its electron density map, is placed on a selected meridian point of the body particularly known to affect the desired tissue. The molecule or electromagnetic field or frequency within the patch reflects a certain electron density which is characteristic to a specific electromagnetic field. The magnitude and direction of the field can be calculated. The field manifested as a certain frequency or a set or frequencies is transmitted to the body in a meridian point. It is well established that the meridian points contain a high concentration of "arranged water" or water clusters. When the electromagnetic frequencies are transmitted to the body in these points, the electromagnetic wave created by the electron density characteristic to the molecule is translated back into clusters that have the same electron density as the original molecule. Thus around the electromagnetic field characteristic to the molecule, there is a concentration of water clusters that imitate the gluthathione molecule in shape, due to their identical electron density map. The momentary cluster progresses along the electron density wave till it reaches the target enzyme, which is the glutathione synthase. At the site of the enzyme the cluster, in the shape of glutathione, binds the active site, and transform the enzyme from its inactive to its active form.

Example 6

Possible Applications of the Water Cluster Theory Disclosed in the Present Invention 1. A novel technology based upon tele-duplication of electronic density on a target plasma printer device, a plasma device or an imprint device.

Such a technology involves communication between computers or cyber communication similar to email. Instead of text, sound or images, the data transferred includes the electron density of an analyzed object.

In accordance with certain embodiments, the device, for example a computer, comprises a plasma unit. The plasma unit comprises an analyzer adapted to analyses electron density of given molecules/objects. The molecules/objects read into the plasma unit are transformed into an electric/magnetic/electromagnetic field which in turn is translated into binary data information, which forms a specific "molecular code". This code is transferred as an email or any other form of communication to another device or computer which has the same unit. The target device or computer includes both an analyzer and a plasma plate which absorbs the electron density information and manifests it into a selected form or substance.

The aforementioned substance may include perfumes, various solutions, drugs and other objects to be encoded and transmitted.

2. Transformation of a smell of a place, for example air of the Himalaya and energy imprint thereof.

In accordance with another aspect of the invention, the mentioned above plasma plate may comprise water cluster forming plate which can transmit the electromagnetic field formed by a specific molecule as a binary data which is translated into an electromagnetic field transformed into a homeopathic solution or directly to a plate connected to the device or computer that would directly be absorbed to the body. This will transfer all homeopathic solutions through the computer. It can activate enzymes to produce essential materials, stimulating the formation of materials by enzymes as melatonin, glutathione, etc. also hormones could be transferred to act at the target Second Part:

Detection Methods Using Terahertz Waves and a System Thereof

The present invention generally pertains to detection methods and systems using electromagnetic waves within the terahertz (THz) range, and more specifically, to means and methods for detection of a pathogen, a cancerous cell or a contaminant using electromagnetic waves within the terahertz (THz) range.

Technologies based on terahertz waves are currently in strong demand in many fields including biochemistry, medicine, environmental science, and security. Advantageous properties such as terahertz transmission through objects opaque to visible light are attracting much attention for spectroscopy and imaging applications.

Terahertz radiation is non-ionizing sub-millimeter electromagnetic wave ranging between mid-infrared and microwave radiation, and shares with microwaves the capability to penetrate a wide variety of non-conducting materials. Terahertz radiation can pass through clothing, paper, cardboard, wood, masonry, plastic and ceramics. It can also penetrate fog and clouds, but cannot penetrate metal or water. During the past decade, THz waves have been used to characterize the electronic, vibrational and compositional properties of solid, liquid, and gas phase materials. The main two applications in which THz fields involved are THz spectroscopy and THz imaging.

Terahertz measurements inevitably require a highly sensitive detector to obtain distinct spectra and images. Nevertheless, the photon energy of the terahertz wave, on the order of millielectron volts (meV), is two to three magnitudes lower than that of the visible light, making the development of a high-performance terahertz detector a difficult task. Another problem with terahertz detection is low spatial resolution of terahertz imaging, which results from the longer wavelengths of terahertz radiation compared to that of visible light. The application of nanoscale materials and devices is opening up new opportunities to overcome these difficulties. Several publications describe various technologies utilizing the characteristics of terahertz waves, for example US Patent Publications No. 2007/0073115, 2008/0014580, 2008/0137068 and 2006/0113298. These publications do not provide practical solutions to food safety monitoring or for controlling the spread of infectious diseases. Assessment of the quality and safety of foods is important in human health. Common pathogenic bacteria that are the causes of food-borne diseases include strains of *Salmonella* and *Escherichia coli* (Sockett 1991). In 1999 it was estimated that foodborne pathogens were responsible for 76 million illnesses annually, resulting in 5,000 deaths [1]. This report identified *Salmonella, Listeria* and *Toxoplasma* as the major causative agents, being responsible for 1,500 of the reported deaths. Data published in 2006 by the CDC suggested that infections due to *Vibrio* have increased [2]. Very recently, an outbreak a food poisoning pathogen found in organic cucumbers has killed at least 14 people in Germany.

Hundreds more have reported serious infections in the outbreak, which could affect tomatoes and lettuce too. Although centered on Germany, where the deaths occurred, the outbreak has spread to Britain, Spain Netherlands and Denmark. It has been reported that the unusual virulent strain of *E. coli* bacteria, *E. coli* serogroup O104 is suspected of being the pathogen likely to be associated with this outbreak. It has been stated by the World Health Organisation office in Europe that the outbreak is unusual in that it has developed very rapidly, and that an unusually high number of cases affected adults instead of the normal high-risk groups, which are young children and the elderly. The conventional microbiological methods for detection of these bacteria, usually include multiple subcultures and biotype- or serotype-identification steps and, thus are laborious and time-consuming (Swaminathan and Feng, 1994; Feng, 1993; Blackburn, 1993). One of the inherent difficulties in the detection of food pathogens is that they are generally present in very low numbers (<100 c.f.u. g-1) in the midst of up to a million or more other bacteria. The advent of gene probe techniques and molecular biology techniques such as genetic amplification methods (i.e. polymerase chain reaction—PCR) and antibody tests (i.e. immunomagnetic separation—IMS) made it possible to relatively reduce assay times while maintaining a high level of sensitivity and specificity. However these methods are still time consuming and require specialized and high costs equipment. The awareness for the possibility of rapid transmittance and worldwide spread of pandemic causing pathogens is also increasing in the last few years. There have been many recent outbreaks of virus infectious epidemics, and some pandemics. In 2003, the SARS virus spread threat created an enormous damage, stopping the whole world normal economy for over one month. The subsequent threat was the H5N1 influenza virus, and later the swine flu virus. Viruses are mutating rapidly and new strands can rapidly create new world pandemic threats 0.3

In the case of swine flu, there was no preparedness, and the virus was rapidly spread worldwide mainly through airports and planes. Thus there is a continuing urgent need for rapid sensitive and noninvasive methods for the detection of viral and bacterial pandemic disease threats, in order to prevent them from rapidly spreading on a worldwide scale and infecting a large proportion of the human population. Terahertz detectors that find dangerous chemicals and weapon are already in use in airport, and are present in the form of gateways that passively read the specific frequencies for chemicals or explosives or guns if a person is carrying them. Therefore a system and method for on-site rapid and easy detection of pathogenic organisms is needed.

Additional Comments Regarding Summary of the Invention

It is therefore one object of the present invention to provide a non-invasive method for detection of a pathogen in a living body using electromagnetic waves within the terahertz (THz) range, wherein said method comprises steps of: (a) obtaining a THz detection stem (TDS); (b) detecting a signal emanating from said pathogen in or on said living body, within the Terahertz frequency range; and, (c) defining at least one characteristic of said pathogen in or on said living body according to said signal. It is a further object of the invention to provide the method as defined above, wherein said characteristic is at least one of presence, absence, concentration and type or serotype. It is a further object of the invention to provide the method as defined above, further comprising a step of detecting said signal passively. It is a further object of the invention to provide the method as defined above, further comprising a step of generating predetermined THz frequency electromagnetic waves specific to resonate with said pathogen. It is a further object of the invention to provide the method as defined above, further comprising a step of directing said waves to said living body to induce a detectable resonant signal from said pathogen.

It is a further object of the invention to provide the method as defined above, further comprising a step of detecting a first electromagnetic wave fingerprint reflected from, or 4 penetrating into or transmitted through said living body which is distinguishable from a second electromagnetic wave fingerprint reflected from or penetrating into or transmitted through a healthy living body.

It is a further object of the invention to provide the method as defined above, further comprising a step of calculating the difference between said first electromagnetic wave fingerprints and said second electromagnetic wave fingerprint.

It is a further object of the invention to provide the method as defined above, further comprising a step of defining at least one characteristic of said pathogen according to a predetermined significance of said difference by applying predetermined parameters or rules.

It is a further object of the invention to provide the method as defined above, further comprising a step of directing electromagnetic waves having a frequency equal to the characteristic frequency of said pathogen so as to detect resonant vibration features of said pathogen.

It is a further object of the invention to provide the method as defined above, further comprising a step of detecting THz frequency electromagnetic waves within the range of about 0.01 THz to about 20 terahertz.

It is a further object of the invention to provide the method as defined above, further comprising a step of detecting THz frequency electromagnetic waves in the wavelength of between about 3 cm and about 3 μm.

It is a further object of the invention to provide the method as defined above, further comprising a step of detecting THz frequency electromagnetic waves in the range of about 0.2 to about 2.2 THz (10 to 79.2 cm-1).

It is a further object of the invention to provide the method as defined above, further comprising a step of detecting THz frequency electromagnetic waves in the range of about 2 cm-1 to about 300 cm-1.

It is a further object of the invention to provide the method as defined above, further comprising a step of detecting THz frequency electromagnetic waves in a range of about 0.2 THz to about 30 THz.

It is a further object of the invention to provide the method as defined above, further comprising a step of detecting THz frequency electromagnetic waves in a range of about 800 THz to about 1200 THz.5

It is a further object of the invention to provide the method as defined above, further comprising a step of detecting predetermined electromagnetic waves in the range of sub THz frequency.

It is a further object of the invention to provide the method as defined above, wherein said pathogen is selected from a group consisting of bacteria, virus, mold, algae, prion, parasite, fungi, spore, microorganism, prokaryotic organism and eukaryotic organism. It is a further object of the invention to provide the method as defined above, wherein said pathogen is selected from a group consisting of Ebola virus, *E. coli*, Methicillin Resistant *Staphylococcus aureus* (MRSA), procalcitonin phenol soluble modulin, anthrax, *Bacillus subtilis* cytomegalovirus (CMV), Human Immunodeficiency Virus (HIV), Human T-cell Lymphotrophic Virus (HTLV), meningitis infection, viral meningitis pneumococcus, SARS, influenza virus, swine influenza virus and H5N1, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, DNA viruses, RNA viruses, viruses possessing single strand RNA, viruses possessing double strand DNA, groups III, IV, V, VI and VII viruses, Phaginae viruses, Phytophaginae and Zoophaginae.

It is a further object of the invention to provide the method as defined above, wherein said fungal infection is selected from a group consisting of *Candida, Cryptococcus neoformans, Aspergillus fumigates*, Blastocladiomycota, chytridiomycota, Dikarya, Glomeromycota, Microsporidia, and Neocallimastigomycota.

It is a further object of the invention to provide the method as defined above, especially adapted for screening and/or detecting pandemic causing pathogens in airport gateways.

It is a further object of the invention to provide the method as defined above, additionally comprising a step of detecting a biological molecule undergoing a physical, biological and/or chemical change.

It is a further object of the invention to provide the method as defined above, further comprising a step of detecting a signal reflected from, penetrating into or transmitted through said living body.

It is a further object of the invention to provide the method as defined above, further comprising a step of generating or detecting THz frequency electromagnetic waves characterized by a pulse or a continuous signal or by a combination thereof.

6 It is a further object of the invention to provide the method as defined above, further comprising a step of detecting the intensity of said signal.

It is a further object of the invention to provide the method as defined above, further comprising a step of detecting a parameter of said signal, said parameter is at least one selected from a group consisting of diffusion, absorption, polarization and chirality.

It is a further object of the invention to provide the method as defined above, further comprising a step of collecting a plurality of THz frequency electromagnetic waves characteristic of a plurality of pathogens into a library, index or database, wherein said library, index or database is used for identification of a specific pathogen in a living body. It is a further object of the invention to provide the method as defined above, further comprising a step of imaging at least a portion of said living body by scanning of THz frequencies.

It is a further object of the invention to provide the method as defined above, further comprising a step of detecting resonance features of hydrogen bonds characteristic of said pathogen.

It is a further object of the present invention to provide a method for detecting a cancerous cell in a biopsy sample using electromagnetic waves within the terahertz (THz) range, wherein said method comprises steps of: (a) obtaining a THz detection system (TDS); (b) detecting a signal, within the Terahertz frequency range, specific to said cancerous cell; and, (c) defining at least one characteristic of said cancerous cell within said biopsy according to said signal.

It is a further object of the invention to provide the method as defined above, wherein said characteristic is at least one of presence, absence, concentration, cell type, differentiation stage and metastatic profile.

It is a further object of the invention to provide the method as defined above, further comprising a step of detecting said signal passively.

It is a further object of the invention to provide the method as defined above, further comprising a step of generating predetermined THz frequency electromagnetic waves specific to resonate with said cancerous cell. It is a further object of the invention to provide the method as defined above, further comprising a step of directing said waves to said biopsy to induce a detectable resonant signal from said cancerous cell.

It is a further object of the invention to provide the method as defined above, further adapted to identify cancerous cells in a living body.

It is a further object of the invention to provide the method as defined above, further adapted to treat cancerous cells within a living body, said method comprises steps of: (a) directing electromagnetic waves within the terahertz (THz) range characteristic of said to said cancerous cell to said living body; and, (c) inducing excitation of said cancerous cells sufficient for said cells to stimulate an immunological effect against said cancerous cells.

It is a further object of the invention to provide the method as defined above, further comprising a step of detecting a first electromagnetic wave fingerprint reflected from, or penetrating into or transmitted through said biopsy which is distinguishable from a second electromagnetic wave fingerprint reflected from or penetrating into or transmitted through a corresponding healthy cell or tissue.

It is a further object of the invention to provide the method as defined above, further comprising a step of calculating the difference between said first electromagnetic wave fingerprints and said second electromagnetic wave fingerprint.

It is a further object of the invention to provide the method as defined above, further comprising a step of defining at least one characteristic of said cancerous cell according to a predetermined significance of said difference by applying predetermined parameters or rules.

It is a further object of the invention to provide the method as defined above, further comprising a step of directing electromagnetic waves having a frequency equal to the characteristic frequency of said cancerous cell so as to detect resonant vibration features of said cancerous cell.

It is a further object of the invention to provide the method as defined above, further comprising a step of detecting THz frequency electromagnetic waves within the range of about 0.01 THz to about 20 terahertz.

It is a further object of the invention to provide the method as defined above, further comprising a step of detecting THz frequency electromagnetic waves in the wavelength of between about 3 cm and about 3 µm.

It is a further object of the invention to provide the method as defined above, further comprising a step of detecting THz frequency electromagnetic waves in the range of about 0.2 to about 2.2 THz (10 to 79.2 cm-1).

It is a further object of the invention to provide the method as defined above, further comprising a step of detecting THz frequency electromagnetic waves in the range of about 2 cm-1 to about 300 cm-1.

It is a further object of the invention to provide the method as defined above, further comprising a step of detecting THz frequency electromagnetic waves in a range of about 0.2 THz to about 30 THz.

It is a further object of the invention to provide the method as defined above, further comprising a step of detecting THz frequency electromagnetic waves in a range of about 800 THz to about 1200 THz.

It is a further object of the invention to provide the method as defined above, further comprising a step of detecting predetermined electromagnetic waves in the range of sub THz frequency.

It is a further object of the invention to provide the method as defined above, wherein said cancerous cell is selected from a group consisting of brain, breast, prostate, colorectum kidney, sarcoma and melanoma.

It is a further object of the invention to provide the method as defined above, wherein said characteristic of said cancerous cell is further selected form a group consisting of altered gene expression, gene mutagenesis, metastasis, apoptosis, programmed cell death, angiogenesis, growth factor regulation, receptor regulation, signal transduction, cell proliferation, cell migration, cell adhesion, cell expansion, cell differentiation, cell invasion, tissue progenitors regulation, cell death, aging process, cellular senescence, carcinogenesis, DNA repair, DNA damage responses, tumorigenesis, anaplasia, abnormal protein synthesis and expression, genomic instability, neoplasia, thrombosis, hyperplasia, dysplasia, aneuploidy, genomic amplification, variation in nuclear size and shape, abnormal tissue organization, growth signals, immortality, mitosis, cell cycle regulation, homeostasis, transcription, haploinsufficiency, telomerase mutations, telomerase mutations, oxidative stress, hypoxia, hyperprolactinemia DNA methylation, pleomorphism, atypia, necrosis, meningitis, astrocytoma, glioblastoma multiforme, and any combination thereof.

It is a further object of the invention to provide the method as defined above, additionally comprising a step of detecting a biological molecule undergoing a physical, biological and/or chemical change.

It is a further object of the invention to provide the method as defined above, further comprising a step of generating or detecting THz frequency electromagnetic waves characterized by a pulse or a continuous signal or by a combination thereof.

It is a further object of the invention to provide the method as defined above, further comprising a step of detecting the intensity of said signal.

It is a further object of the invention to provide the method as defined above, further comprising a step of detecting a parameter of said signal, said parameter is at least one selected from a group consisting of diffusion, absorption, polarization and chirality.

It is a further object of the invention to provide the method as defined above, further comprising a step of collecting a plurality of THz frequency electromagnetic waves characteristic of a plurality of cancerous cells into a library, index or database, wherein said library, index or database is used for identification of a specific cancerous cell in a biopsy or a living body.

It is a further object of the invention to provide the method as defined above, further comprising a step of imaging said cancerous cell by scanning of THz frequencies.

It is a further object of the invention to provide the method as defined above, further comprising a step of detecting resonance features of hydrogen bonds characteristic of said cancerous cell.

It is a further object of the present invention to provide a method for detecting a contaminant in a medical device or surgical or medical set using electromagnetic waves within the terahertz (THz) range, wherein said method comprises steps of: (a) obtaining a THz detection system (TDS); (b) detecting a signal, within the Terahertz frequency range, specific to said contaminant; and, (c) defining at least one characteristic of said contaminant in said medical device or surgical or medical set according to said signal.

It is a further object of the invention to provide the method as defined above, wherein said characteristic is at least one of presence, absence, concentration and type of said contaminant.

It is a further object of the present invention to provide a method for decontaminating a medical device or surgical or medical set from a contaminant using electromagnetic waves within the terahertz (THz) range, wherein said method comprises steps of generating a signal, within the Terahertz frequency range, specific to said contaminant wherein said signal disrupts said contaminant.

It is a further object of the invention to provide the method as defined above, further comprises a step of directing electromagnetic waves within the terahertz (THz) range which are either in direct or in inverse correlation with at least one characteristic of the signal specific to said contaminant.

It is a further object of the invention to provide the method as defined above, further comprising a step of detecting said signal passively.

It is a further object of the invention to provide the method as defined above, further comprising a step of generating predetermined THz frequency electromagnetic waves specific to resonate with said contaminant.

It is a further object of the invention to provide the method as defined above, further comprising a step of directing said waves to said medical device or surgical or medical set to induce a detectable resonant signal from said contaminant.

It is a further object of the invention to provide the method as defined above, further comprising a step of detecting a characteristic of said contaminant, said characteristic is at least one selected from a group consisting of transmittance, absorbance, reflectance, chirality and a phase shift.

It is a further object of the invention to provide the method as defined above, further comprises a step of detecting a first electromagnetic wave fingerprint reflected from, or penetrating into or transmitted through said medical device or surgical or medical set which is distinguishable from a second electromagnetic wave fingerprint reflected from or penetrating into or transmitted through a corresponding uninfected medical device or surgical or medical set.

It is a further object of the invention to provide the method as defined above, further comprising a step of calculating the difference between said first electromagnetic wave fingerprints and said second electromagnetic wave fingerprint.

It is a further object of the invention to provide the method as defined above, further comprising a step of defining at least one characteristic of said contaminant according to a predetermined significance of said difference by applying predetermined parameters or rules.

It is a further object of the invention to provide the method as defined above, further comprising a step of detecting THz frequency electromagnetic waves in the range of about 0.01 THz to about 20 terahertz.

It is a further object of the invention to provide the method as defined above, further comprising a step of detecting THz frequency electromagnetic waves in the wavelength of between about 3 cm and about 3 µm.

It is a further object of the invention to provide the method as defined above, further comprising a step of detecting THz frequency electromagnetic waves in the range of about 0.2 to about 2.2 THz (10 to 79.2 cm-1).

It is a further object of the invention to provide the method as defined above, further comprising a step of detecting THz frequency electromagnetic waves in the range of about 2 cm-1 to about 300 cm-1.

It is a further object of the invention to provide the method as defined above, further comprising a step of detecting THz frequency electromagnetic waves in a range of about 0.2 THz to about 30 THz, alternatively in a range of about 800 THz to about 1200 THz.

It is a further object of the invention to provide the method as defined above, further comprising a step of detecting electromagnetic waves in the range of sub THz frequency.

It is a further object of the invention to provide the method as defined above, wherein said contaminant is either a living contaminant or a nonliving contaminant.

It is a further object of the invention to provide the method as defined above, wherein said nonliving contaminant is at least one of organic contaminant, inorganic contaminant, biochemical molecule, chemical analyte, or a biochemical analyte.

It is a further object of the invention to provide the method as defined above, wherein said inorganic contaminant is selected from a group consisting of metal, salt and debris.

It is a further object of the invention to provide the method as defined above, wherein said living contaminant is at least one of bacteria, virus, mold, algae, prion, parasite, fungi, spore microorganism, prokaryotic organism and eukaryotic organism.

It is a further object of the invention to provide the method as defined above, wherein said biochemical molecule is selected from a group consisting of an antigen, a toxin, a parasite, an allergen, a DNA molecule, a RNA molecule, nucleotides, a protein, a lipid, a glycolipid, an enzyme, a tissue mass, cells, a hormone, a neurotransmitter.

It is a further object of the invention to provide the method as defined above, additionally comprising a step of detecting a contaminant undergoing a physical, biological and/or chemical change.

It is a further object of the invention to provide the method as defined above, further comprising a step of generating or detecting THz frequency electromagnetic waves characterized by a pulse or a continuous signal or by a combination thereof.

It is a further object of the invention to provide the method as defined above, further comprising a step of detecting the intensity of said signal.

It is a further object of the invention to provide the method as defined above, further comprising a step of imaging said medical device or surgical or medical set by scanning of THz frequencies.

It is a further object of the present invention to provide a method for detection of a contaminant in an (Heating, Ventilation, and Air Conditioning) HVAC and/or water supply or drainage system using electromagnetic waves within the terahertz (THz) range, wherein said method comprises steps of: (a) obtaining a THz detection system (TDS); (b) detecting a signal, within the Terahertz frequency range, specific to said contaminant; and, (c) defining a characteristic of said contaminant in said HVAC and/or water supply or drainage system according to said signal.

It is a further object of the invention to provide the method as defined above, wherein said characteristic is at least one of presence, absence, concentration and type of said contaminant.

It is a further object of the invention to provide the method as defined above, further comprising a step of detecting said signal passively.

It is a further object of the invention to provide the method as defined above, further comprising a step of generating predetermined THz frequency electromagnetic waves specific to resonate with said contaminant.

It is a further object of the invention to provide the method as defined above, further comprising a step of directing said waves to said HVAC and/or water supply or drainage system to induce a detectable resonant signal from said contaminant.

It is a further object of the invention to provide the method as defined above, further comprising a step of detecting a first electromagnetic wave fingerprint reflected from, or penetrating into or transmitted through said HVAC and/or water supply or drainage system which is distinguishable from a second electromagnetic wave fingerprint reflected from, or penetrating into or transmitted through a reference HVAC and/or water supply or drainage system as a control.

It is a further object of the invention to provide the method as defined above, further comprising a step of calculating the difference between said first electromagnetic wave fingerprints and said second electromagnetic wave fingerprint.

It is a further object of the invention to provide the method as defined above, further comprising a step of defining the at least one characteristic of said contaminant according to a predetermined significance of said difference by applying predetermined parameters or rules.

It is a further object of the invention to provide the method as defined above, further comprising a step of directing electromagnetic waves having a frequency equal to the characteristic frequency of said contaminant so as to detect resonant vibration of said contaminant.

It is a further object of the invention to provide the method as defined above, further comprising a step of detecting THz frequency electromagnetic waves in the range of about 0.01 THz to about 20 terahertz.

It is a further object of the invention to provide the method as defined above, further comprising a step of detecting THz frequency electromagnetic waves in the wavelength of between about 3 cm and about 3 μm.

It is a further object of the invention to provide the method as defined above, further comprising a step of detecting THz frequency electromagnetic waves in the range of about 0.2 to about 2.2 THz (10 to 79.2 cm-1).

It is a further object of the invention to provide the method as defined above, further comprising a step of detecting THz frequency electromagnetic waves in the range of about 2 cm-1 to about 300 cm-1.

It is a further object of the invention to provide the method as defined above, further comprising a step of detecting THz frequency electromagnetic waves in a range of about 0.2 THz to about 30 THz, alternatively in a range of about 800 THz to about 1200 THz.

It is a further object of the invention to provide the method as defined above, further comprising a step of detecting electromagnetic waves in the range of sub THz frequency.

It is a further object of the invention to provide the method as defined above, further comprising a step of detecting a contaminant within HVAC and/or water supply or drainage system containing liquid, solid, gas, powder, slurry, paste, concentrate, water-miscible, water-immiscible, aggregated solutions, dispersions, emulsions, solution, particles, industrial fluid and mixtures thereof.

It is a further object of the invention to provide the method as defined above, wherein said industrial fluid is selected from a group consisting of engine oil, petroleum, soap and cooling water, pool water.

It is a further object of the invention to provide the method as defined above, further adapted for detecting a contaminant in HVAC and/or water supply or drainage system in a public domain including planes, ships, healthcare centers and airports.

It is a further object of the invention to provide the method as defined above, further comprising a step of detecting said contaminant within pipes, tubes, conduits, cylinder, tunnel, circulating systems, coils.

It is a further object of the invention to provide the method as defined above, wherein said contaminant is either a living contaminant or a nonliving contaminant.

It is a further object of the invention to provide the method as defined above, wherein said nonliving contaminant is at least one of organic contaminant, inorganic contaminant, biochemical molecule, chemical analyte, biochemical analyte or biomarker.

It is a further object of the invention to provide the method as defined above, wherein said inorganic contaminant is selected from a group consisting of metal, salt and debris.

It is a further object of the invention to provide the method as defined above, wherein said living contaminant is at least one of bacteria, virus, mold, algae, prion, parasite, fungi, spore, microorganism, prokaryotic organism and eukaryotic organism, mite, insect and nematode, yeast.

It is a further object of the invention to provide the method as defined above, wherein said living contaminant is selected from a group consisting of Methicillin Resistant *Staphylococcus aureus* (MRSA), procalcitonin phenol soluble modulin, anthrax, *Bacillus subtillus* (BG), cytomegalovirus (CMV), Ebola Virus, Human Immunodeficiency Virus (HIV), Human T-cell Lymphotrophic Virus (HTLV), meningitis infection, viral meningitis pneumococcus, *Legionella pneumophila, Pseudomonas aeruginosa, Cladosporium cladosporioides, Stachybotrys chartarum, Penicillium corylyphilum* and Endotoxin, Reoviridae, Picornaviridae, Caliciviridae, Togaviridae, Arenaviridae, Flaviviridae, rthomyxoviridae, Paramyxoviridae, Bunyaviridae, Rhabdoviridae, Filoviridae, Coronaviridae, Astroviridae, Bornaviridae, Arteriviridae, DNA viruses, RNA viruses, viruses possessing single strand RNA, viruses possessing double strand DNA, groups III, IV, V, VI and VII viruses, Phaginae viruses, Phytophaginae and Zoophaginae.

It is a further object of the invention to provide the method as defined above, wherein said fungal infection is selected from a group consisting of *Candida, Cryptococcus neoformans, Aspergillus* fumigates, Blastocladiomycota, chytridiomycota, Dikarya, Glomeromycota, Microsporidia, and Neocallimastigomycota.

It is a further object of the invention to provide the method as defined above, wherein said biochemical molecule is selected from a group consisting of an antigen, a toxin, a parasite, an allergen, a DNA molecule, a RNA molecule, nucleotides, a protein, a lipid, a glycolipid, an enzyme, a tissue mass, cells, a hormone, a neurotransmitter.

It is a further object of the invention to provide the method as defined above, additionally comprising a step of detecting a contaminant undergoing a physical, biological and/or chemical change.

It is a further object of the present invention to provide a method for detection of a contaminant in a food or beverage sample using electromagnetic waves within the terahertz (THz) range, wherein said method comprises steps of: (a) obtaining a THz detection system (TDS); (b) detecting a signal, within the Terahertz frequency range, specific to said contaminant; and, (c) defining a characteristic of said contaminant within said food or beverage sample according to said signal.

It is a further object of the invention to provide the method as defined above, wherein said characteristic is at least one of presence, absence, concentration and type of said contaminant.

It is a further object of the invention to provide the method as defined above, further comprising a step of detecting said signal passively.

It is a further object of the invention to provide the method as defined above, further comprising a step of generating predetermined THz frequency electromagnetic waves specific to resonate with said pathogen.

It is a further object of the invention to provide the method as defined above, further comprising a step of directing said waves to said food or beverage sample to induce a detectable resonant signal from said contaminant.

It is a further object of the invention to provide the method as defined above, further comprising a step of directing said waves to said food or beverage sample to induce a detectable resonant signal from said contaminant.

It is a further object of the invention to provide the method as defined above, further comprising a step of detecting a first electromagnetic wave fingerprint reflected from, or penetrating into or transmitted through said affected food or beverage sample which is distinguishable from a second electromagnetic wave fingerprint reflected from or penetrating into or transmitted through a corresponding uninfected food sample.

It is a further object of the invention to provide the method as defined above, further comprising a step of calculating the difference between said first electromagnetic wave fingerprints and said second electromagnetic wave fingerprint.

It is a further object of the invention to provide the method as defined above, further comprising a step of defining at least one characteristic of said contaminant according to a predetermined significance of said difference by applying predetermined parameters or rules.

It is a further object of the invention to provide the method as defined above, further comprising a step of detecting THz frequency electromagnetic waves in the range of about 0.01 THz to about 20 terahertz.

It is a further object of the invention to provide the method as defined above, further comprising a step of detecting THz frequency electromagnetic waves in the wavelength of between about 3 cm and about 3 μm.

It is a further object of the invention to provide the method as defined above, further comprising a step of detecting THz frequency electromagnetic waves in the range of about 0.2 to about 2.2 THz (10 to 79.2 cm-1).

It is a further object of the invention to provide the method as defined above, further comprising a step of detecting THz frequency electromagnetic waves in the range of about 2 cm-1 to about 300 cm-1.

It is a further object of the invention to provide the method as defined above, further comprising a step of detecting THz frequency electromagnetic waves in a range of about 0.2 THz to about 30 THz, alternatively in a range of about 800 THz to about 1200 THz.

It is a further object of the invention to provide the method as defined above, further comprising a step of detecting electromagnetic waves in the range of sub THz frequency. It is a further object of the invention to provide the method as defined above, further comprising a step of on line detection of a contaminant in a sample selected from a group consisting of a food product, a food additive, a therapeutic product, a beverage, an edible liquid, a non-edible liquid, a cosmetic product, an industrial fluid.

It is a further object of the invention to provide the method as defined above, further comprising a step of selecting the form of said sample from a group consisting of liquid, solid, gas, powder, slurry, paste, concentrate, water-miscible, water-immiscible, aggregated solutions, dispersions, emulsions, solution, particles and mixtures thereof.

It is a further object of the invention to provide the method as defined above, wherein said food is selected from a group consisting of a vegetable or a processed vegetable product, a fruit or a processed fruit product a meat or a meat product, fish or fish product or egg or egg product.

It is a further object of the invention to provide the method as defined above, wherein said meat or meat product is selected from a group consisting of beef, raw ground beef, pork, chicken and red meat.

It is a further object of the invention to provide the method as defined above, wherein said beverage is a fruit juice or a vegetable juice.

It is a further object of the invention to provide the method as defined above, wherein said contaminant is either a living contaminant or a nonliving contaminant.

It is a further object of the invention to provide the method as defined above, wherein said non-living contaminant is at least one of organic contaminant, inorganic contaminant, biochemical molecule, chemical analyte, biochemical analyte or biomarker.

It is a further object of the invention to provide the method as defined above, wherein said inorganic contaminant is selected from a group consisting of metal, salt and debris.

It is a further object of the invention to provide the method as defined above, wherein said living contaminant is at least one of bacteria, virus, mold, algae, prion, parasite, fungi, spore, microorganism, prokaryotic organism and eukaryotic organism.

It is a further object of the invention to provide the method as defined above, wherein said contaminant is a food borne pathogen.

It is a further object of the invention to provide the method as defined above, wherein said food born pathogen is a pathogen selected from a group consisting of *E. coli*, *E. coli* serogroup O104, *Escherichia coli* O104:H4, anthrax, *Streptococcus pyogenes*, scarlet fever causing bacteria, *Salmonella* serotypes, *Staphylococcus aureus*, *Campylobacter jejuni*, *Campylobacter coli*, enterotoxigenic *E. coli*, enteroinvasive *Escherichia coli*, *Clostridium perfringens*, *Bacillus cereus*, *Yersinia enterocolitica*, *Listeria monocytogenes*, *E. coli* O157:H7, *Aeromonas* spp., *Plesiomonas* spp., *Shigella*, enterohemorrhagic *Escherichia coli*, Coliform. Yeast, Moulds, Streptococci *Campylobacter*, *Bacillus cereus*, *Clostridium*, mesophilic aerobic bacteria, *Pseudomonas* spp., Enterobacteriaceae, lactic acid bacteria, *Enterococcus* spp., enteritis *Vibrio* and a combination thereof.

It is a further object of the invention to provide the method as defined above, wherein said biochemical molecule is selected from a group consisting of an antigen, a toxin, a parasite, an allergen, a DNA molecule, a RNA molecule, nucleotides, a protein, a lipid, a glycolipide, an enzyme, a tissue mass, cells, a hormone, a neurotransmitter.

It is a further object of the invention to provide the method as defined above, especially adapted to be performed in a continuous production process or a batch production process.

It is a further object of the invention to provide the method as defined above, additionally comprising a step of determining at least one parameter characteristic of said food sample, said at least one parameter is selected from a group consisting of size, size distribution, shape, Brix, viscosity, density, Aw water content, water hardness boiling point, refractive index, viscosity, moisture content, acidity, rheologic properties, magnetic properties, conductivity, pH, oxygen content, permittivity, permeability or dielectric constant or any other characteristic of said food or beverage sample.

It is a further object of the invention to provide the method as defined above, additionally comprising a step of detecting a contaminant undergoing a physical, biological and/or chemical change.

It is a further object of the invention to provide the method as defined above, especially adapted for an industrial process selected from a group consisting of food processing industry, pharmaceutics industry, cosmetics industry, paper industry, petroleum industry, water industry or pollution monitoring industry, sewage treatment.

It is a further object of the invention to provide the method as defined above, further adapted for controlling water pollution.

It is a further object of the invention to provide the method as defined above, further comprising a step of detecting the intensity of said signal.

It is a further object of the invention to provide the method as defined above, further comprising a step of collecting a plurality of resonant THz frequency electromagnetic waves into a library, index or database, wherein said library, index or database is used for identification of a contaminant in a food or beverage sample.

It is a further object of the invention to provide the method as defined above, further comprising a step of imaging said food or beverage sample by scanning of THz frequencies.

It is a further object of the invention to provide the method as defined above, further comprising a step of detecting a characteristic of said contaminant, said characteristic is at least one selected from a group consisting of transmittance, absorbance, reflectance and a phase shift.

It is a further object of the invention to provide the method as defined above, further comprising a step of detecting resonance features of hydrogen bonds characteristic of said contaminant.

It is a further object of the present invention to provide a method for monitoring a predetermined environmental factor using electromagnetic waves within the terahertz (THz) range comprising steps of: (a) obtaining a THz detection system (TDS); (b) detecting a signal emanating from said environmental factor, within the Terahertz frequency range; and, (c) defining at least one characteristic of said environmental factor according to said signal.

It is a further object of the invention to provide the method as defined above, further comprising a step of detecting an insect or pest, preferably bedbug or flea.

It is a further object of the present invention to provide a method of generating a database or index useful for rapid identification of a contaminant using electromagnetic waves within the terahertz (THz) range, comprising steps of:
  a. obtaining a system for detection of a contaminant using electromagnetic waves within the terahertz (THz) range, comprising; i. detection means for detecting a signal emanating from said contaminant, within the Terahertz frequency range; and,
  ii. processing means for defining at least one characteristic of said contaminant according to said signal;
    b. receiving data from said system;
    c. collecting said data on a retrievable data base; d. receiving an automatically generated indexing code related to said data; and e. storing said collected data or an indication of the data on a retrievable database useful for rapid identification of a contaminant using electromagnetic waves within the terahertz (THz) range.

It is a further object of the present invention to provide a database or index useful for rapid identification of a contaminant, said database or index comprising stored data on electromagnetic waves within the terahertz (THz) range specific to resonate with predetermined list of contaminants.

It is a further object of the present invention to provide a THz detection system (TDS) for detection of a contaminant, or a cancerous cell or a pathogen using electromagnetic waves within the terahertz (THz) range, comprising:
  a. detection means for detecting a signal emanating from said contaminant, cancerous cell or pathogen within the Terahertz frequency range; and,
  b. processing means for defining at least one characteristic of said contaminant, cancerous cell or pathogen according to said signal.

It is a further object of the invention to provide the system as defined above, further comprising:
  a. an electromagnetic wave generation unit configured to generate an electromagnetic wave in a predetermined THz frequency specific to resonate with said contaminant, cancerous cell or pathogen;
  b. irradiation means configured to irradiate said wave to induce a detectable resonate signal from said contaminant, cancerous cell or pathogen;
  c. detection means for detecting said resonate signal;
  d. processing and/or outputting means for defining at least one characteristic of said contaminant, cancerous cell or pathogen according to said resonant signal.

It is a further object of the present invention to provide a method of inducing a biological effect comprising steps of transmitting electromagnetic waves within the terahertz (THz) range to a mammal, wherein said electromagnetic waves are characterized by predetermined THz frequency electromagnetic waves specific to a biological, biochemical or chemical molecule and/or the hydrogen bonds which are characteristic of said biological, biochemical or chemical molecule so as to induce a signal specific to said biological, biochemical or chemical molecule or said hydrogen bonds characteristic of said biological, biochemical or chemical molecule, thereby inducing a biological effect.

Additional Comments Regarding Description of Specific Embodiments of the Invention The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide means and methods for detection of a pathogen, a cancerous cell or a contaminant using electromagnetic waves within the terahertz (THz) range.

The terahertz (THz) band of the electromagnetic spectrum lies in the frequency interval from 0.1 to 10 THz (3 mm to 30 μm in wavelength), bridging the gap between the infrared and microwave bands. It is herein submitted that there are unique characteristics of the THz wave that make it a powerful technique in sensing and imaging. The THz wave is characterized by non-ionizing radiation (in contrast to penetrating radiation using higher energies), that is highly absorbed by polar molecules, making it very sensitive to water. In addition, the THz radiation penetrates many physical barriers such as typical clothing and packing material. Thus the THz technique used in the present invention uniquely combine safe-to-use high-resolution imaging and identification through spectroscopy, contaminants such as chemical substances and biological agents such as pathogens including bacteria and viruses and cancerous cells.

The nondestructive THz method and system of the present invention is also applied to food and agricultural industry.

The present invention provides detection methods using electromagnetic waves within the terahertz (THz) range. The aforementioned methods are useful for medical and food applications as detailed in the following disclosure:

It is one aspect of the present invention to provide a non-invasive method for detection of a pathogen in a living body using electromagnetic waves within the terahertz (THz) range. The aforesaid method comprises steps of: (a) obtaining a THz detection system (TDS) (b) detecting a signal emanating from said pathogen in or on said living body, within the Terahertz frequency range; and, (c) defining at least one characteristic of said pathogen in or on said living body according to said signal.

It is a further aspect of the present invention to provide a method for detecting a cancerous cell in a biopsy sample using electromagnetic waves within the terahertz (THz) range. The aforesaid method comprises steps of: (a) obtaining a THz detection system (TDS); (b) detecting a signal, within the Terahertz frequency range, specific to said cancerous cell; and, (c) defining at least one characteristic of said cancerous cell within said biopsy according to said signal.

It is a further aspect of the present invention to provide a method for detecting a contaminant in a medical device or surgical or medical set including plastic lines and tubes, using electromagnetic waves within the terahertz (THz) range. The aforesaid method comprises steps of (a) obtaining a THz detection system (TDS); (b) detecting a signal, within the Terahertz frequency range, specific to said contaminant; and, (c) defining at least one characteristic of said contaminant in said medical device or surgical or medical set according to said signal.

It is a further aspect of the present invention to provide a method for decontaminating a medical device or surgical or medical set from a contaminant using electromagnetic waves within the terahertz (THz) range, comprising steps of generating a signal, within the Terahertz frequency range, specific to said contaminant, wherein the signal disrupts the contaminant. It is a further aspect of the present invention to provide a method for detection of a contaminant in an (Heating, Ventilation, and Air Conditioning) HVAC and/or water supply or drainage system using electromagnetic waves within the terahertz (THz) range. The aforesaid method comprises steps of: (a) obtaining a THz detection system (TDS); (b) detecting a signal, within the Terahertz frequency range, specific to said contaminant; and, (c) defining a characteristic of said contaminant in said HVAC and/or water supply or drainage system according to said signal.

It is a further aspect of the invention to provide a method for detection of a contaminant in a food or beverage sample using electromagnetic waves within the terahertz (THz) range, wherein the method comprises steps of: (a) obtaining a THz detection system (TDS); (b) detecting a signal, within the Terahertz frequency range, specific to said contaminant; and, (c) defining a characteristic of said contaminant within said food or beverage sample according to said signal.

It is within the scope of the present invention to disclose the aforementioned methods, wherein the characteristic defined by applying the THz detection methods may include at least one of presence, absence, concentration type or serotype of the pathogen, or cancerous cell or contaminant detected.

According to one embodiment of the invention, the detection of the signal by the aforementioned methods is performed passively. As used herein the term 'passive detection' refers to detection of spontaneous THz photons or signal by a passive detector or scanner. The signal is emanated or received from the pathogen or cancerous cell or contaminant to be detected by the aforementioned methods.

Alternatively, the detection of the signal by the aforementioned methods is performed actively, by irradiating predetermined electromagnetic waves within the THz range.

It is therefore a further aspect of the invention to provide the aforementioned methods, further comprising a step of generating predetermined THz frequency electromagnetic waves specific to resonate with the pathogen, or cancerous cell or contaminant to be detected. It is also within the scope of the invention to provide the aforementioned methods further comprising a step of directing the THz waves to one of the following: living body, biopsy, medical device or surgical or medical set, HVAC and/or water supply or drainage system or food or beverage sample to induce a detectable resonant signal from the pathogen, or cancerous cell or contaminant.

It is also within the scope of the invention to provide the aforementioned methods, further comprising a step of detecting a first electromagnetic wave fingerprint reflected from, penetrating into or transmitted through the living body, biopsy, medical device or surgical or medical set, HVAC and/or water supply or drainage system or food or beverage sample. The aforementioned first electromagnetic wave fingerprint is preferably distinguishable from a second control or reference electromagnetic wave fingerprint reflected from or penetrating into or transmitted through the same.

It is also within the scope of the present invention to provide the methods, further comprising a step of calculating the difference between the first electromagnetic wave fingerprint and the second electromagnetic wave fingerprint.

It is a further main aspect of the invention to provide the aforementioned methods, further comprising a step of defining the at least one characteristic according to a predetermined significance of the above mentioned difference by applying predetermined parameters or rules.

The term 'significance' used herein generally refers to the statistical significance of the signal to noise ratio, or more specifically to the extent to which a result deviates from an experiment, i.e. the calculated difference between the first electromagnetic wave fingerprint and the second electromagnetic wave fingerprint, is expected to arise simply from random variation or errors in sampling. In other words the significance of an event refers to the probability of the occurrence of the event. The significance value is calculated by applying predetermined parameters or rules.

According to certain embodiments of the invention, the significance level refers to a predetermined value in the range of 0.01-0.08.

Thus the method disclosed in the present invention allows effective detection in real time and on site of a pathogen, a cancerous cell or a contaminant with a safer and less invasive system using electromagnetic waves within the terahertz range.

According to certain embodiments of the present invention, a beam of THz rays is irradiated towards objects or at a living organism, i.e. few meters away, then the rays reflected from, penetrating into or transmitted through the object or living are measured and checked against a database of spectroscopic signatures or fingerprints.

In accordance with a further embodiment of the invention, the aforementioned method further comprises a step of directing electromagnetic waves having a frequency equal to the characteristic frequency of the pathogen, cancerous cell or contaminant so as to detect resonant vibration of the pathogen, cancerous cell or contaminant.

As used herein, the term 'contaminant' refers in the present invention to any undesirable or unwanted constituent that is either present in an environment where it does not belong or is present at levels that might cause harmful effects to humans or to the environment. More specifically, a contaminant can also refer to a biological, chemical, physical, or radiological substance which, in sufficient concentration, can adversely affect living organisms through air, water, soil, edible or non-edible liquid, industrial fluid and/or food. Such contaminants may include pesticide residue, veterinary drug residue, herbicide residue, additives, aflatoxin and food borne pathogens. In certain embodiments of the invention a contaminant might be a living or a non-living substance. According to some aspects of the present invention, a contaminant can also mean impure poisonous or polluting substance often at the trace level, or any mixtures of the above mentioned substances. The term 'pathogen' used herein refers in a non-limiting manner to bacteria, virus, mold, algae, prion, parasite, fungi, spore, microorganism, prokaryotic organism and eukaryotic organism. More specifically a pathogen within the scope of the present invention may include bacteria species such as *E. coli, E. coli* serogroup O104, *Escherichia coli* O104:H4, Methicillin Resistant *Staphylococcus aureus* (MRSA), anthrax, *Bacillus subtilis*; procalcitonin phenol soluble modulin; viral groups, types, families and species and such as ytomegalovirus (CMV), Ebola Virus, retrovirus, Human Immunodeficiency Virus (HIV), Human T-cell Lymnphotrophic Virus (HTLV), meningitis infection, viral meningitis pneumococcus, SARS, influenza virus, swine influenza virus and H5N1, Reoviridae, Reovirus, Rotavirus, Picornaviridae, Enterovirus, Rhinovirus, Hepatovirus, Cardiovirus, Aphthovirus, Poliovirus, Parechovirus, Erbovirus, Kobuvirus, Teschovirus, Coxsackie, Caliciviridae Norwalk virus, Hepatitis E virus, Togaviridae, Rubella virus, Arenaviridae, Lymphocytic choriomeningitis virus, Flaviviridae, Dengue virus, Hepatitis C virus, Hepatitis B virus Yellow fever virus, Orthomyxoviridae, Influenzavirus A, Influenzavirus B, Influenzavirus C, Isavirus, Thogotovirus, Paramyxoviridae, Measles virus, Mumps virus, Respiratory syncytial virus, Rinderpest virus, Canine distemper virus, Bunyaviridae, Calif. encephalitis virus, Hantavirus, Rhabdoviridae Rabies virus, Filoviridae, Ebola virus, Marburg virus, Coronaviridae, Corona virus, Astroviridae, Astrovirus, Bornaviridae, Borna disease virus, Arteriviridae, Arterivirus, Equine Arteritis Virus, DNA viruses, RNA viruses, viruses possessing single strand RNA, viruses possessing double strand DNA, groups III, IV, V, VI and VII viruses, Phaginae viruses (infect bacteria), Phytophaginae (infect plants) and Zoophaginae (infect animals). A fungal infection may include but it is not limited *Candida, Cryptococcus neoformans, Aspergillus* fumigates, Blastocladiomycota, chytridiomycota, Dikarya, Glomeromycota, Microsporidia, and Neocallimastigomycota.

The term 'cancerous cell' may also refer to tumor cells, neoplasm, cancer stem cells and oncology. Cancerous cells as disclosed in the present invention may include head/neck cells, digestive system cells, respiratory system cells, bone cells, skin cells, blood cells, urogenital cells, nervous system cells and endocrine system cells. Types of cancerous cell with respect to histology may include carcinoma, sarcoma, papilloma and adenoma. The term 'on line' used hereinafter refers to the immediate performance of the described method and system of the present invention adapted for immediate use and availability, avoiding human intervention. According to further aspects of the invention, the term on line can also mean a continuous control of a product stream or process, for example detecting a contaminant, as described above, in a food or beverage sample.

The term 'biological change' or 'chemical change' refers in the present invention to any enzymatic, hormonal, pathological, microbiological such as biocide, ripping change, oxidation state, reduction state, pH, concentration changes of soluble or otherwise dispersed compositions, water activity, etc.

The term 'state transformation' refers in the present invention to any physical, electrochemical, chemical and/or biological state transformations and changes, including biological changes and chemical changes.

The term 'plurality' applies hereinafter to any integer greater than or equal to one.

The term 'Terahertz (THz) range' used herein refers to electromagnetic waves propagating at frequencies in the terahertz range. It is synonymously termed sub millimeter radiation, terahertz waves, terahertz light, T-rays, T-light, T-lux or THz. The term typically applies to electromagnetic radiation with frequencies between high-frequency edge of the microwave band, 300 gigahertz ($3 \times 10^{11}$ Hz), and the long-wavelength edge of far-infrared light, 3000 GHz ($3 \times 10^{12}$ Hz or 3 THz). The THz region of the electromagnetic spectrum lies in the frequency interval from 0.1 to 10 THz. In wavelengths, this range corresponds to 0.03 mm (or 30 μm) infrared to 3.0 mm microwave.

According to one embodiment of the present invention, the predetermined THz frequency electromagnetic waves are in the range of about 0.01 THz to about 20 terahertz, preferably in the range of about 0.2 to about 2.2 THz (10 to 79.2 $cm^{-1}$). In another embodiment, the predetermined THz frequency electromagnetic waves are in a range of about 0.2 THz to about 30 THz. It is also within the scope of the invention that the THz frequency electromagnetic wave is in a range of about 800 THz to about 1200 THz.

According to a further embodiment of the present invention, the predetermined THz frequency electromagnetic waves are in the wavelength of between about 3 cm and about 3 μm. It is also within the scope of the present invention that the predetermined THz frequency electromagnetic waves in the range of about 2 $cm^{-1}$ to about 300 $cm^{-1}$.

According to a further embodiment of the present invention, the predetermined electromagnetic waves are in the range of sub THz frequency.

It is according to a further embodiment of the current invention to present a method comprising the step of or the steps of in-line and on-line detection of a contaminant infecting a food or beverage sample using electromagnetic waves within the terahertz (THz) range especially adapted to be performed along the production line and hence avoiding slowing down the manufacturing process.

It is according to a further embodiment of the current invention to present a method especially adapted for inspecting the presence i.e. the concentration and the identification of at least one predetermined material or contaminant in a food or beverage sample, as well as its characteristic selected from size, size distribution, particles shape, a w, water content, shape, Brix, viscosity, density, water content, water hardness, boiling point, refractive index, viscosity, moisture content, acidity, rheologic properties, magnetic properties, conductivity, pH, oxygen content, conductivity, permittivity, permeability or dielectric constant or any other characteristic. The aforesaid characteristics may be applied to a food or beverage sample.

It is also an object of the invention to use the methods and system of the present invention to detect the presence of a specific material in a fluid. The fluid composition itself can be any type of fluid, such as a solution, a liquid containing suspended particulates, or, in some embodiments, even a gas phase containing a particular chemical or a mixture of chemicals. It can also include a liquid composition undergoing a physical and/or chemical change.

In other embodiments of the invention, the online detection system and method of the present invention is adapted to detect a contaminant in an edible or non-edible liquid.

According to a further embodiment of the invention, the detected sample may comprise at least one form selected from a group including liquid, solid, gas, powder, slurry, paste, concentrate, water-miscible, water-immiscible, aggregated solutions, dispersions, emulsions, solution, particles and mixtures thereof.

According to a further embodiment of the invention, the food sample is a meat or a meat product, fish or fish product or egg or egg product. In certain embodiments, the meat is selected from a group including beef, raw ground beef, pork, chicken and red meat.

In certain embodiments, the method as described above is adapted for food inspection. The present invention provides a method and THz detection system (TDS) to detect the content of food material, to discern adulterated food and to detect poison and food borne pathogens in food products. According to one aspect, the food sample contains a vegetable selected from a group including green vegetables, root vegetables, tuberous and organically grown vegetables. In other embodiments a fruit is selected from citrus, fleshy fruits, botanical fruits, aggregate fruit and seedless fruits.

According to a further embodiment of the invention the beverage sample may be a fruit juice or a vegetable juice.

It is also within the scope of the present invention that the detected sample is an industrial fluid, preferably selected in a non-limiting manner from a group including engine oil, petroleum, soap and cooling water.

In other embodiments of the invention, the detected sample is a non-edible liquid that may include at least one of sea water, pool water, cooling water and fluids in Heating, Ventilation, and Air Conditioning (HVAC) systems.

The system and method of the present invention may also be applied to detecting a contaminant within HVAC systems and/or water supply or drainage systems especially those systems located in crowded or closed public domains such as planes or ships, medical centers, where safe and healthy conditions are regulated by controlling air quality parameters, including temperature, humidity, ventilation, air infiltration and maintenance of pressure distribution between spaces by indoor systems (i.e. HVAC) as well as "fresh air" from outdoors. It is therefore a further aspect of the invention to provide method and system for on line detection of a contaminant within HVAC systems using electromagnetic waves within the terahertz (THz) range. In some embodiments the detection of the contaminant may be performed within pipes, tubes or conduits.

In a further aspect of the invention, the contaminant may be either a living contaminant or a non-living contaminant.

According to certain embodiments of the invention, the non-living contaminant may be at least one of organic contaminant, inorganic contaminant biochemical molecule, chemical analyte, biochemical analyte or biomarker. More specifically, an inorganic contaminant may in a non-limiting manner be one of metal, salt and debris.

According to other embodiments, a living contaminant may be at least one of bacteria, virus, mold, algae, prion, parasite, fungi, spore, microorganism, prokaryotic organism and eukaryotic organism. More particularly, the living contaminant is a food borne pathogen.

Examples of a food born pathogen within the scope of the present invention include a pathogen selected from a group comprising *E. coli*, anthrax, *Streptococcus pyogenes*, scarlet fever causing bacteria, *Salmonella* serotypes, *Staphylococcus aureus*, *Campylobacter jejuni*, *Campylobacter coli*, enterotoxigenic *E. coli*, enteroinvasive *Escherichia coli*, *Clostridium perfringens*, *Bacillus cereus*, *Yersinia enterocolitica*, *Listeria monocytogenes*, *E. coli* O157:H7, *Aeromonas* spp., *Plesiomonas* spp., *Shigella*, enterohemorrhagic *Escherichia coli*, Coliform. Yeast, Moulds, Streptococci *Campylobacter, Bacillus cereus, Clostridium*, mesophilic aerobic bacteria, *Pseudomonas* spp., Enterobacteriaceae, lactic acid bacteria, *Enterococcus* spp., enteritis *Vibrio* and a combination thereof.

In further embodiments the living contaminant is a pathogen selected from a group consisting of Methicillin Resistant *Staphylococcus aureus* (MRSA), procalcitonin phenol soluble modulin, cytomegalovirus (CMV), Ebola Virus, Human Immunodeficiency Virus (HIV), Human T-cell Lymphotrophic Virus (HTLV), meningitis infection, viral meningitis pneumococcus and melatonin pathway.

According to a further embodiment of the invention, a biochemical molecule detected by the method of the present invention may an antigen, a toxin, a parasite, an allergen, a DNA molecule, a RNA molecule, nucleotides, a protein, a lipid, a glycolipide, an enzyme, a tissue mass, cells, a hormone, a neurotransmitter.

In certain embodiments, examples of neurotransmitters may include amino acids such as glutamate, aspartate, D-serine, γ-aminobutyric acid (GAB A) and glycine, monoamines and other biogenic amines such as dopamine (DA), norepinephrine (noradrenaline; NE, NA), epinephrine (adrenaline), histamine and serotonin (SE, 5-HT) and other neurotransmitters such as acetylcholine (ACh), adenosine, anandamide and nitric oxide. The THz detection system of the present invention can detect the presence, concentration and relative amounts and concentrations of neurotransmitters in a sample or living body.

The present invention further provides a method for monitoring a predetermined environmental factor using electromagnetic waves within the terahertz (THz) range. The aforementioned method comprises steps of: (a) detecting a signal emanating from said environmental factor, within the Terahertz frequency range; and, (b) defining at least one characteristic of said environmental factor according to said signal.

According to one embodiment, the aforesaid method further comprises a step of detecting an insect or pest, preferably bedbug or flea.

The present invention further provides a method of generating a database or index useful for rapid identification of a contaminant using electromagnetic waves within the terahertz (THz) range. The aforesaid method comprises steps of: (a) obtaining a system for detection of a contaminant using electromagnetic waves within the terahertz (THz) range; (b) receiving data from said system; (c) collecting said data on a retrievable data base; (d) receiving an automatically generated indexing code related to said data; and (e) storing said collected data or an indication of the data on a retrievable database useful for rapid identification of a contaminant using electromagnetic waves within the terahertz (THz) range. In a main embodiment of the invention the system as mentioned above comprises (a) detection means for detecting a signal emanating from said contaminant, within the Terahertz frequency range; and, (b) processing means for defining at least one characteristic of said contaminant according to said signal.

The present invention further provides a database or index useful for rapid identification of a contaminant, the database or index comprising stored data on electromagnetic waves within the terahertz (THz) range specific to resonate with predetermined list of contaminants.

The present invention further provides a non-invasive THz detection system (TDS) for detection of a pathogen, a cancerous cell or a contaminant using electromagnetic waves within the terahertz (THz) range. The aforesaid system comprises: (a) detection means for detecting a signal emanating from said contaminant, within the Terahertz frequency range; and, (b) processing means for defining at least one characteristic of said contaminant according to said signal.

In accordance with certain embodiments of the invention the system as described above further comprises: (a) an electromagnetic wave generation unit configured to generate an electromagnetic wave in a predetermined THz frequency specific to resonate with said contaminant; (b) irradiation means configured to irradiate said wave to induce a detectable resonate signal from said contaminant; (c) detection means for detecting said resonate signal from said contaminant; and, (d) processing/outputting means for defining at least one characteristic of said contaminant according to said resonant signal.

It is also within the scope of the present invention to provide a method of inducing a biological effect. The aforementioned method comprises steps of transmitting electromagnetic waves within the terahertz (THz) range to a mammal, wherein the electromagnetic waves are characterized by predetermined THz frequency electromagnetic waves specific to a biological, biochemical or chemical molecule and/or the hydrogen bonds which are characteristic of said biological, biochemical or chemical molecule so as to induce a signal specific to said biological, biochemical or chemical molecule or said hydrogen bonds characteristic of said biological, biochemical or chemical molecule, thereby inducing a biological effect.

Various examples were carried out to prove the embodiments claimed in the present invention. Some of these experiments are referred hereinafter. The examples describe the manner and process of the present invention and set forth the best mode contemplated by the inventors for carrying out the invention, but are not to be construed as limiting the invention.

EXAMPLES OF THE TERAHERTZ TECHNOLOGY

Example 1

Detection of a Pandemic Causing Pathogen in Public Areas

The non-invasive detection method of the present invention provides a tool for rapid and sensitive detection of a viral and/or bacterial infectious disease in a living body, and thereby preventing the spread of these pathogens, especially in public domains such as hospitals, airplanes and airports. The detection according to the present invention may be used for the following applications:

A direct detection of infected persons using passive or active terahertz detection provides an example of an application of the present invention. The detection may be performed by applying predetermined THz wavelength, i.e. in the range of about 890 to about 910 THz.

The present invention provides a detector and method for detecting specific frequencies of viruses and pathogens according to a terahertz index. The THz detector produces specific terahertz signals that correspond to specific wave length of the pathogens.

The detection may be performed actively or passively.

The term active detection as used herein refers to transmitting a specific terahertz frequency towards a living body or a sample (i.e. saliva sample of the person suspected in carrying the pathogen) or object that is suspected to contain the pathogen or contaminant to be detected. A resonant signal is detected in the case where the transmitted frequency is identical to the frequency of the detected pathogen or contaminant.

Alternatively the resonance signal can be detected by physical methods, for example, by measuring a change of conductivity, or resistance in a checking point in the body.

Example 2

Detection of a Contaminant within HVAC Systems

A detection method and system as described above is used for continuous monitoring of airway or HVAC systems in a plane, ship, medical or healthcare center and/or airports. A signaling or an alert is transmitted to a monitoring center when a pathogen of danger is present.

Airway systems in public places, especially in public places controlled or monitored by closed air circulation systems are prone to be a major route in which contaminants and/or pathogenic diseases are rapidly and easily spread.

Detection of a contaminant within HVAC systems using the detection system and method of the present invention may be performed within samples obtained from the i.e. airway system, collected using a gas sample collector, and read by the THz detection system in predetermined time intervals.

Methicillin-resistant *Staphylococcus aureus* (MRSA) is an example of a bacterium which is responsible for several difficult-to-treat infections in humans, especially in confined environments such as prisons, airplanes and ships. Many MRSA infections occur in hospitals and healthcare facilities, with a higher incidence rate in nursing homes or long-term care facilities, where patients with open wounds, invasive devices and weakened immune systems are at greater risk of infection than the general public.

The present invention provides a method and system for detecting a contaminant or a pathogen in HVAC systems of hospitals and healthcare facilities. These systems which control indoor air quality parameters, including temperature, humidity, ventilation, air infiltration and maintenance of pressure distribution between spaces as well as "fresh air" from outdoors, may be the main cause for transmitting infectious diseases such as diseases 33 caused by the MRSA bacterium. By monitoring the tubes in HVAC systems of hospitals using the THz detector and detection method as disclosed above, with frequencies or wave length established by the present invention to detect the desirable pathogen or contaminant, prevention of the spread of the infectious disease is achieved. The transmittance of an infectious disease in healthcare facilities could be executed by using contaminated invasive medical devices or surgical or medical sets. The present invention further provides a system and method for detection of a contaminant or a pathogen in a medical device or surgical or medical set, before and after being in contact with the patient.

Such a procedure, using passive or active detection or scanning of a specific contaminant or a pathogen can be routinely used when treating a patient with infusion, catheter or any other invasive device or procedure in hospitals or elderly houses. This feature of the invention is used to detect and treat dangerous and highly infective pathogens such as the MRSA bacteria.

In order to treat an infectious pathogen or contaminant detected in a medical device or surgical or medical set, it is within the scope of the present disclosure to provide a method for decontaminating a medical device or surgical or medical set from a contaminant using electromagnetic waves within the terahertz (THz) range. The aforesaid method comprises steps of generating a signal, within the Terahertz frequency range, specific to the contaminant wherein the signal disrupts the contaminant. An example of such a sterilization procedure may include irradiating the medical device or surgical or medical set with THz frequencies or wavelength characterized by an opposite phase with respect to the frequencies or wavelength specific to the pathogen of interest, such that the generated THz frequencies or wavelength disrupt the pathogen.

Example 3

Detection and Treatment of Cancerous Cells

It is herein acknowledged that cancer cells have specific terahertz frequencies resulting from their RNA strands. Each tumor has its own fingerprint terahertz frequency. The THz detector and the detection methods of the present invention, can distinguish between different types and differentiation states of cancer cells, between migrating cells that would cause metastases and localized cells. An example of such a procedure may contain the following stages: a sample obtained from a cancerous tissue of a person after surgery, or a biopsy, is subjected to cell separation, using various techniques known in the art. The separated cells are being read for predetermined THz frequencies characteristic to different cancerous cell types, using a passive terahertz detector or using an emitting-receiving detector for active THz detection A patch containing the characteristic frequency of the cancer cell, or several frequencies that correspond to all cell types, or the tumor in general, is prepared, using active pumping submission. The patch is placed on the person with the specific tumor, preferably on the patient's skin close to a meridian point. The submitted specific tumor frequency resonates with migrating cells, thus causing the cancer cell to be in an excited state. In this state the immune system may recognize the cells and exterminate them. By using the above described method, the creation of new metastases is prevented.

In order to disrupt predetermined cancer cells, in a tumor mass, THz frequencies characterized by inverse or complementary phase, relative to the frequency or wavelength phase used for the detection of the cancerous cells, are submitted to the tissue or biopsy. In certain embodiments, the THz frequencies are transmitted through a patch as described above. Such a procedure causes extermination of the tumor cell, which may lead to the tumor cell death.

Example 4

Using Electromagnetic Waves as Drug Replacements (Rational Homeopathy)

Reference is now made to electromagnetic frequency replacement of small molecules that activate or inhibit biological molecules.

Without wishing to be bound by theory, the following is herein acknowledged: water molecules have the property of creating clusters that mimic the shape of specific molecules. This property is attributed to the hydrogen bonds that are formed between adjacent water molecules. An example for such property may be found in the biotin-avidin extensively investigated complex. The biotin molecule is being mimicked by a 5 water molecule cluster that resembles the overall structure of biotin. This cluster is arranged in the binding site of the free avidin causing it to change its conformation from the free-unbound to the bound state.

X ray structure of the water cluster of the biotin avidine complex, compared to an x ray structure of biotin-avidine complex has revealed that although the structures of the biotin and 5 water molecule cluster is similar, and not completely identical the electron density of biotin and the 5 molecule cluster are completely identical.

The term electron density refers to the molecular-electrical feature that creates electromagnetic wave directed, preferably in perpendicular to the direction of the rotating electrons. Each wave is characterized by a direction, amplitude and frequency that is specific to the electron density of the specific molecule. Thus it is herein emphasized that the electromagnetic wave which is formed by a certain molecule is common to the molecule, and is also common to the water cluster that mimics its structure. Terahertz frequencies are of special importance in this regard, because they are the in the energy frequency range of hydrogen bonds formed within water clusters, and protein structures. Very recently, a terahertz detector has been used to detect the folding process of a protein by scanning the change in its terahertz frequencies. This type of detector is used herein to identify the exact frequencies of specific molecules and the water clusters that mimic those molecules.

The herein disclosed THz detector and detection method are further used for mimicking drug molecules aimed at certain targets, by predetermined electromagnetic waves that create specific water clusters within the body.

Thus by submitting a specific wave length in a meridian point in the body (for example through a patch) a cluster may be formed in the microenvironment of the wave which is similar to the original molecule characteristic wave length. The wave is progressed in the body, by the water clusters that are formed around it that resembles the wave which is characteristic to the original molecule. Upon approaching the target enzyme or molecule, the cluster reaches the active site of the target enzyme or molecule, and thus changes the conformation of the protein from the resting state to the active state, where it can perform its action. For example, the enzyme glutathione synthase produces the molecule glutathione. By attaching a patch containing glutathione to a person, the electromagnetic wave frequency characteristic of glutathione, is transmitted to the body, and induces the formation of water clusters that activate glutathione synthase. It is shown that by using the THz detector and detection method of the present invention, the production of glutathione synthase increased by about 400 fold relative to a naturally occurring control process. Similar results were obtained by applying the same procedure as described above to the production of melatonin by melatonin synthase.

It is within the scope of the present invention to provide a data base of terahertz frequencies of a plurality of drugs or biological molecules. It is further emphasized that such methods as described above are herein refer to rational homeopathy or rational personal homeopathy. The herein disclosed method and system can be effectively used to mimic the activity of predetermined drugs and may replace the need of using toxic chemicals to treat people.

Example 5

Detection of a Food Born Pathogen In Vitro

A predetermined pathogen, such as *salmonella* or *E. coli* is inoculated into an embryonic chicken egg. A standard procedure for introduction of a pathogen into an embryonic chicken egg can be, injecting a selected pathogen into pathogen-free eggs 11-12 days after fertilization. The pathogen is then allowed to replicate by placing the inoculated eggs at 37 degrees C. for 48 hours. A THz detector as described above is used to transmit predetermined electromagnetic waves within the THz range of 0.2 to 2.2 THz, or in the range of 10-25 cm-1, toward the infected egg to detect a resonant signal from the pathogen. The detected signal is distinguishable from a signal produced by transmitting electromagnetic waves within the same frequency toward corresponding pathogen-free embryonic chicken eggs.

Example 6

Detection of a Food Born Pathogen in a Meat Sample

A THz detection system as described above is used for detection and identification of a food born pathogen in a meat sample.

A measuring probe equipped with an analyzer is placed adjacent to a meat sample. The aforementioned apparatus is calibrated and adjusted to a resonance frequency for a given selected pathogen. On-line measure of the meat sample around the calibrated resonance frequency is performed. The variation between the measured value and the standard one (performed on a corresponding isolated pathogen) enables detection of a contaminant within the meat sample. It is appreciated that such a system can be implemented at various points in the supply chain, from the abattoir to the supermarket or butchery.

Example 7

Detection of a Food Born Pathogen in Vegetables

A THz detection system as described above is used for detection and identification of a food born pathogen in vegetables.

A THz detection system (TDS) is placed adjacent to an industrial conveyor line of a selected vegetable. The aforementioned apparatus is calibrated and adjusted to a resonance frequency for a given selected pathogen or specific chemicals including vitamins, sugars, pharmaceuticals, agricultural chemicals, etc. discovered in the THz wave region.

Alternatively, analysis of the vegetable sample or production line is made by a passive THz detection of molecular bonds present that can give details of the types of molecules present in the food. On-line measure of the vegetable sample around the calibrated resonance frequency, or using electromagnetic waves within the terahertz (THz) range is performed. The detected signal received from the sample or the variation between the measured value and the standard one (performed on a corresponding isolated pathogen or chemical molecule) enables detection of a contaminant within the vegetable sample. Thus the present invention provides a rapid, accurate, sensitive and economical method available to the food industry or compositional analysis.

Example 8

Detection of a Contaminant within a Liquid Sample

Performing water quality monitoring on the water stream, by using a THz detection system disclosed in the present invention. The variation of the measured value from the standard one enables detection of the water composition change. An alert is activated if the system detects a predetermined significant change.

The water monitoring can be used for homeland security in the event of a spilling a poison, or chemical or biological contaminant. While most of the existing detection technologies can detect contaminants at very low concentrations, they are often specific to one contaminant or a group of contaminants. Because the physical and chemical properties of potential contaminants can vary greatly, instruments that measure one contaminant or a small subset of possible contaminants is of little use because that contaminant may not be the one used. Most of the biological monitors, such as the use of algae, had limited distribution system. Monitors that use fish or mussels can detect cyanide and chlorinated pesticides, but not at the desired detection limit. A measuring probe equipped with an analyzer is placed on water well and is calibrated and adjusted to a resonance frequency for a given potable water solution such that a reference is created. A smith chart was measured and the measurement on the resonant frequency was recorded. Each different composition has a different response. On-line measure around the resonance frequency is continuously performed on the water stream or water sample performing water quality monitoring. The variation of the measured value from the standard one enables detection of the water composition change. An alert is activated if the system detects a predetermined significant change.

Example 9

Detection of a Contaminant on a Ketchup Production Line

A measuring probe equipped with an analyzer is placed on a ketchup production line and is calibrated and adjusted to a resonance frequency for a given ketchup viscosity. A smith chart was measured and the measurement on the resonant frequency was recorded. On-line and in-line measure of the smith chart around the resonance frequency is continuously performed on the ketchup stream. On line information e.g. water quantity or water activity Aw is available in the control room enabling either automatically or manually immediate response. An alert may be activated if the system detects a predetermined significant change having precision of about 0.5%, in order to lower or to higher the water quantity on-line and in-line, such that a predetermined standard viscosity according to the customer requirements and preferences is obtained.

Example 10

Detection of a Contaminant of a Grain Stream

The system also provides an automated and non-invasive monitoring on grain stream. The information of the grain monitoring is used to establish the quality characteristics and the value of the grain. The monitoring is also necessary for proper grain storage management.

Information from the grain, such as grain moisture content and the amount of foreign material, can be used to determine appropriate action to maintain the quality of the stored product. The distribution of constituents is generally not uniform throughout the load; the constituents of the grain mass stratify and segregate. This causes variations in the physical characteristics within the load. The air space between the grain constituents cause leaps in the measurement. The method of monitoring is therefore extremely important to ensure that the grain stream is truly representative of the whole grain mass. The frequency per unit volume of grain is measured. A smith chart is of measured and the measurement on the resonant frequency is recorded. The information about the obtained grain moisture is the average moisture of the whole grain mass.

Examples

Example 1: A method of identifying the presence of a pathogen in an individual said method comprising steps of:
  a. making a first recording (R1) of at least one parameter of a body portion of said individual;
  b. transmitting a set of impulses characteristic of said pathogen to said body portion;

c. making a second recording (R2) of said specific parameters after said transmitting of said set of impulses; and,
d. determining the difference between R2 relative to R1 wherein said difference is indicative of the presence of said pathogen in said individual.

Example 2: The method according to example 1, wherein said parameters and/or said impulses are electromagnetic frequencies.

Example 3: The method according to example 1, further comprising steps of detecting the presence or absence of electromagnetic resonance, said electromagnetic resonance is characterized by said difference between R2 and R1, further wherein said presence of said pathogen is correlated with the presence or absence of said electromagnetic resonance.

Example 4: The method according to example 1 additionally comprising steps of selecting said parameters from a group comprising electromagnetic frequency, conductivity, muscle resistance, electrical resistance, electric current, direct current, surface tension, potential, electromagnetic radiation, wavelength, spectroscopic fingerprint, a transcutaneous electrical nerve stimulation, a Fourier transform infrared spectroscopy (FTIR), a Nuclear magnetic resonance (NMR) or a combination thereof.

Example 5: The method according to example 1 additionally comprising steps of recording said at least one parameter using a device selected from a group comprising a Zapper, a Bicom, a tensiometer, a SCS-BARS device, a David Tansley transposer, a galvanometer, a Flu master, a Direct Current (DC) resistant meter, a current reading device, a Rife device, a global diagnostics devise, an FTIR spectrometer, an NMR spectrometer, MRI device, an imaging device, a tuning fork device or any combination thereof.

Example 6: The method according to example 1 additionally comprising steps of obtaining said set of specific parameters using kinesiology and radiometry methods.

Example 7: The method according to example 1 additionally comprising steps of determining the difference between R2 relative to R1 wherein said difference is in the range of about 10% to about 25% reduction in R2 relative to R1.

Example 8: The method according to example 1 additionally comprising steps of identifying the presence of a pathogen selected from a group comprising viruses, bacteria, parasites, fungi, allergens, toxins or a combination thereof.

Example 9: The method according to example 1 additionally comprising steps of transmitting said set of impulses characteristic to said body portion using a signal generator device.

Example 10: The method according to example 9, additionally comprising steps of selecting said signal generating device from a group comprising a Zapper, a Bicom, a Flu master, a David Tansley transposer, a transponder, a transducer, an electromagnetic signal generator, a Rife device, a global diagnostics devise, a tuning fork or a combination thereof Electromagnetic Frequencies are in the range of 0.1-20000 Hertz.

Example 11: The method according to example 1 additionally comprising steps of transmitting said set of impulses to said body portion in a contactless manner or without physical contact.

Example 12: The method according to example 1 additionally comprising steps of transmitting said set of impulses to said body portion in a remote manner.

Example 13: The method according to example 1 additionally comprising steps of transmitting said set of impulses to said body portion from a substrate.

Example 14: The method according to example 13 additionally comprising steps of selecting said substrate from a group comprising a pad, a pillow, a patch, a strip, a disk, a medium, a support or a combination thereof.

Example 15: The method according to example 13, additionally comprising steps of incorporating said pathogen within said substrate.

Example 16: The method according to example 13, additionally comprising steps of transmitting said set of impulses to said body portion from a substrate preprogrammed with the impulses characteristic to said pathogen.

Example 17: The method according to example 16, additionally comprising steps of preprogramming said substrate by implementing a software or disc within said substrate, said software or disc contain said impulses characteristic to said pathogen.

Example 18: The method according to example 16, additionally comprising steps of preprogramming said substrate by a remotely controlled device adapted to produce said impulses characteristic to said pathogen.

Example 19: The method according to example 18, additionally comprising steps of preprogramming said substrate by a remotely controlled device adapted to produce said impulses characteristic to said pathogen according to a predetermined data base.

Example 20: The method according to example 13 additionally comprising steps of applying said substrate to said body portion of said individual.

Example 21: The method according to example 1 additionally comprising steps of selecting said body portion from a group comprising meridian points, acupuncture points, internal part of the palm, foot, neck, reflexology map or atlas, a conventional anatomy map or a combination thereof.

Example 22: A method of identifying tumor cells in an individual said method comprising steps of:
a. making a first recording (R1) of a set of specific parameters of a body portion of said individual;
b. transmitting a set of impulses characteristic of said pathogen to said body portion;
c. making a second recording (R2) of said specific parameters after said transmitting of said set of impulses; and,
d. determining the difference between R2 relative to R1 wherein said difference is indicative of the presence of said tumor cells in said individual.

Example 23: The method according to example 22 additionally comprising steps of identifying tumor cells selected from a group selected from the Rife Index.

Example 24: A method of treating tumor cells in an individual said method comprising steps of:
a. making a first recording (R1) of a set of specific parameters of a body portion of said individual;
b. transmitting a set of impulses characteristic of said pathogen to said body portion;
c. making a second recording (R2) of said specific parameters after said transmitting of said set of impulses; and, d. Determining the difference between R2 relative to R1 wherein said difference is indicative of the presence of said tumor cells further wherein said difference causes excitation of said tumor cells sufficient for said cells to stimulate an immunological effect against said tumor cells.

Example 25: A system useful for identifying the presence of a pathogen in an individual said system comprising:
  a. means for making a first recording (R1) of a set of specific parameters of a body portion of said individual;
  b. means for transmitting a set of impulses which correspond to characteristics of said pathogen to said body portion; and,
  c. means for making a second recording (R2) of said specific parameters after said transmitting of said set of impulses, wherein the difference between R2 relative to R1 is indicative of the presence of said pathogen.

Example 26: The system according to example 25, wherein said parameters and/or said impulses are electromagnetic frequencies.

Example 27: The system according to example 25, wherein said system is adapted to detect the presence or absence of electromagnetic resonance, said electromagnetic resonance is characterized by said difference between R2 and R1, further wherein said presence of said pathogen is correlated with the presence or absence of said electromagnetic resonance.

Example 28: The system according to example 25, wherein said parameters are selected from a group comprising electromagnetic frequency, conductivity, muscle resistance, electrical resistance, electric current, direct current, surface tension, potential, electromagnetic radiation, wavelength, spectroscopic fingerprint, a transcutaneous electrical nerve stimulation, a Fourier transform infrared spectroscopy (FTIR), a Nuclear magnetic resonance (NMR) or a combination thereof.

Example 29: The system according to example 25, wherein said means for recording said specific parameters are selected from a group comprising a Zapper, a Bicom, a tensiometer, a David Tansley transposer, a galvanometer, a Flu master, a Direct Current (DC) resistant meter, a current reading device, an FTIR spectrometer, an NMR spectrometer, MRI device, an imaging device, a tuning fork device, or a combination thereof.

Example 30: The system according to example 25, wherein said system is further adapted to obtain said set of specific parameters using kinesiology and radiometry methods.

Example 31: The system according to example 25, wherein said difference between R2 relative to R1 is in the rage of about 10% to about 25% reduction in R2 relative to R1.

Example 32: The system according to example 25, wherein said pathogen is selected from a group comprising viruses, bacteria, parasites, fungi, allergens, toxins or a combination thereof.

Example 33: The system according to example 25, wherein said transmitting means further comprise a signal generating device.

Example 34: The system according to example 33, wherein said signal generating device is selected from a group comprising a Zapper, a Bicom, a Flu master, a David Tansley transposer, a transponder, transducer, electromagnetic signal generator, a Rife machine, a tuning fork or a combination thereof.

Example 35: The system according to example 25, wherein said set of impulses is transmitted to said body portion in a contactless manner or without physical contact.

Example 36: The system according to example 25, wherein said set of impulses is transmitted to said body portion in a remote manner.

Example 37: The system according to example 25, wherein said means for transmitting said set of impulses further comprise a substrate adapted to transmit said set of impulses to said body portion.

Example 38: The system according to example 37, wherein said substrate is selected from a group comprising a pad, a pillow, a patch, a strip, a disk, a medium, a support or a combination thereof.

Example 39: The system according to example 37, wherein said pathogen is incorporated within said substrate.

Example 40: The system according to example 37, wherein said substrate is preprogrammed according to said impulses characteristic to said pathogen.

Example 41: The system according to example 40, wherein said substrate is preprogrammed by software or disc implemented within said substrate, said software or disc contain said impulses characteristic to said pathogen.

Example 42: The system according to example 40, wherein said substrate is preprogrammed by a remotely controlled device adapted to produce said impulses characteristic to said pathogen.

Example 43: The system according to example 40, wherein said substrate is preprogrammed by a remotely controlled device adapted to produce said impulses characteristic to said pathogen according to a predetermined data base.

Example 44: The system according to example 25, wherein said transmitting means further adapted to produce electromagnetic frequencies characteristic of said pathogen.

Example 45: The system according to example 37, wherein said substrate is applied to said body portion of said individual.

Example 46: The system according to example 25, wherein said body portion is selected from a group comprising meridian points, acupuncture points, internal part of the palm, foot, neck, reflexology map or atlas, a conventional anatomy map or a combination thereof.

Example 47: A system useful for identifying tumor cells in an individual said system comprising:
  a. means for making a first recording (R1) of a set of specific parameters of a body portion of said individual;
  b. means for transmitting a set of impulses characteristic of said pathogen to said body portion; and,
  c. means for making a second recording (R2) of said specific parameters after said transmitting of said set of impulses; wherein the difference between R2 relative to R1 is indicative of the presence of said tumor cells in said individual.

Example 48: The system according to example 47, wherein said tumor cells are selected from a group selected from the Rife Index.

Example 49: A system useful for treating tumor cells in an individual said system comprising:

a. means for making a first recording (R1) of a set of specific parameters of a body portion of said individual;
b. means for transmitting a set of impulses characteristic of said pathogen to said body portion; and,
c. means for making a second recording (R2) of said specific parameters after said transmitting of said set of impulses, wherein the difference between R2 relative to R1 is indicative of the presence of said tumor cells further wherein said difference causes excitation of said tumor cells sufficient for said cells to stimulate an immunological effect against said tumor cells.

Example 50: A method for inducing a protective immune response in an individual against a pathogen, said method comprising steps of transmitting a set of impulses characteristic of said pathogen to a body portion, wherein said impulses provokes a cascade reaction sufficient for said pathogen to stimulate an immunological effect against said pathogen.

Example 51: A method of early stage prevention of the spread of a contagious disease caused by a pathogen, said method comprising steps of:
a. making a first recording (R1) of at least one parameter of a body portion of said individual;
b. transmitting a set of impulses characteristic of said pathogen to said body portion;
c. making a second recording (R2) of said specific parameters after said transmitting of said set of impulses;
d. determining the difference between R2 relative to R1 wherein said difference is indicative of the presence of said pathogen; and,
e. isolating said individual so as to prevent the spread of said contagious disease.

Example 52: A method useful for rapidly screening and identifying the presence of a contagious disease caused by a pathogen, said method comprising steps of:
a. making a first recording (R1) of at least one parameter of a body portion of said individual;
b. transmitting a set of impulses characteristic of said pathogen to said body portion;
c. making a second recording (R2) of said specific parameters after said transmitting of said set of impulses;
d. determining the difference between R2 relative to R1 wherein said difference is indicative of the presence of said pathogen in an individual; and,
e. repeating steps a to d in a plurality of individuals, thereby rapidly screening and identifying the presence of a contagious disease caused by said pathogen.

Example 53: A screening system for early detection of a pathogen in an individual, said system comprising:
a. means for making a first recording (R1) of a set of specific parameters of a body portion of said individual;
b. means for transmitting a set of impulses which correspond to characteristics of said pathogen to said body portion; and,
c. means for making a second recording (R2) of said specific parameters after said transmitting of said set of impulses, wherein the difference between R2 relative to R1 is indicative of the presence of said pathogen in said individual.

Example 54: A method for creating or updating a data base, said data base comprising at least one parameter characteristic to at least one pathogen, said method comprising steps of:
a, making a first recording (R1) of at least one parameter of a body portion of said individual;
b. transmitting a set of impulses or parameters characteristic of a tested pathogen to said body portion;
c. making a second recording (R2) of said specific parameters after said transmitting of said set of impulses;
d. determining the difference between R2 relative to R1 wherein said difference is indicative of the presence of said tested pathogen in said individual; and,
e. adding said set of impulses or parameters characteristic of said tested pathogen to said data base.

Example 55: A method for inducing a cellular response by predetermined activating a molecule in an individual, said method comprising steps of:
a. exposing a body portion of said individual to said activating molecule or to impulses/electron density field/arrangement characteristic of said activating molecule; and,
b. transmitting a set of impulses characteristic of said molecule to said body portion, wherein said impulses provoke a response or cascade or reaction sufficient for said molecule to stimulate a cellular response.

Example 56: A method according to example 55, additionally comprising steps of selecting said molecule from a group comprising hormones, transcription factors, enzymes, nucleic acids, proteins or a combination thereof.

Example 57: A method according to example 55, additionally comprising steps of selecting said cellular response cascade/reaction from a group comprising enzymatic reactions, hormonal reactions, gene translation reactions, cell proliferation, DNA replication, cell death reactions or a combination thereof.

Example 58: A method according to example 55, additionally comprising steps of selecting said body portion form a group comprising meridian points, acupuncture points, internal part of the palm, foot, neck, reflexology map or atlas, a conventional anatomy map or a combination thereof.

Example 59: A non-invasive method for detection of a pathogen in a living body using electromagnetic waves within the terahertz (THz) range, wherein said method comprises steps of:
a. obtaining a THz detection system (TDS);
b. detecting a signal emanating from said pathogen in or on said living body, within the Terahertz frequency range; and,
c. defining at least one characteristic of said pathogen in or on said living body according to said signal.

Example 60. The method according to example 59, wherein said characteristic is at least one of presence, absence, concentration and type or serotype.

Example 61. The method according to example 59, further comprising a step of detecting said signal passively.

Example 62. Predetermined THz frequency electromagnetic waves specific to resonate with said pathogen.

Example 63. The method according to example 59, further comprising a step of directing said waves to said living body to induce a detectable resonant signal from said pathogen.

Example 64. The method according to example 59, further comprising a step of detecting a first electromagnetic wave fingerprint reflected from, or penetrating into or transmitted through said living body which is distinguishable from a second electromagnetic wave fingerprint reflected from or penetrating into or transmitted through a healthy living body.

Example 65. The method according to example 64, further comprising a step of calculating the difference between said first electromagnetic wave fingerprint and said second electromagnetic wave fingerprint.

Example 66. The method according to example 65, further comprising a step of defining at least one characteristic of said pathogen according to a predetermined significance of said difference by applying predetermined parameters or rules.

Example 67. The method according to example 59, further comprising a step of directing electromagnetic waves having a frequency equal to the characteristic frequency of said pathogen so as to detect resonant vibration features of said pathogen.

Example 68. The method according to example 59, further comprising a step of detecting THz frequency electromagnetic waves within the range of about 0.01 THz to about 20 terahertz.

Example 69. The method according to example 59, further comprising a step of detecting THz frequency electromagnetic waves in the wavelength of between about 3 cm and about 3 μm.

Example 70. The method according to example 59, further comprising a step of detecting THz frequency electromagnetic waves in the range of about 0.2 to about 2.2 THz (10 to 79.2 cm-1).

Example 71. The method according to example 59, further comprising a step of detecting THz frequency electromagnetic waves in the range of about 2 cm-1 to about 300 cm-1.

Example 72. The method according to example 59, further comprising a step of detecting THz frequency electromagnetic waves in a range of about 0.2 THz to about 30 THz.

Example 73. The method according to example 59, further comprising a step of detecting THz frequency electromagnetic waves in a range of about 800 THz to about 1200 THz.

Example 74. The method according to example 59, further comprising a step of detecting predetermined electromagnetic waves in the range of sub THz frequency.

Example 75. The method according to example 59, wherein said pathogen is selected from a group consisting of bacteria, virus, mold, algae, prion, parasite, fungi, spore, microorganism, prokaryotic organism and eukaryotic organism.

Example 76. The method according to example 75, wherein said pathogen is selected from a group consisting of *E. coli*, Methicillin Resistant *Staphylococcus aureus* (MRSA), procalcitonin phenol soluble modulin, anthrax, *Bacillus subtilis*, Ebola virus, cytomegalovirus (CMV), Human Immunodeficiency Virus (HIV), Human T-cell Lymphotrophic Virus (HTLV), meningitis infection, viral meningitis pneumococcus, SARS, influenza virus, swine influenza virus and H5N1, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, DNA viruses, RNA viruses, viruses possessing single strand RNA, viruses possessing double strand DNA, groups III, IV, V, VI and VII viruses, Phaginae viruses, Phytophaginae and Zoophaginae.

Example 77. The method according to example 75, wherein said fungal infection is selected from a group consisting of *Candida, Cryptococcus neoformans, Aspergillus* fumigates, Blastocladiomycota, chytridiomycota, Dikarya, Glomeromycota, Microsporidia, and Neocallimastigomycota.

Example 78. The method according to example 59, especially adapted for screening and/or detecting pandemic causing pathogens in airport gateways.

Example 79. The method according to example 59, additionally comprising a step of detecting a biological molecule undergoing a physical, biological and/or chemical change.

Example 80. The method according to example 59, further comprising a step of detecting a signal reflected from, penetrating into or transmitted through said living body.

Example 81. The method according to example 59, further comprising a step of generating or detecting THz frequency electromagnetic waves characterized by a pulse or a continuous signal or by a combination thereof.

Example 82. The method according to example 59, further comprising a step of detecting the intensity of said signal.

Example 83. The method according to example 59, further comprising a step of detecting a parameter of said signal, said parameter is at least one selected from a group consisting of diffusion, absorption, polarization and chirality.

Example 84. The method according to example 59, further comprising a step of collecting a plurality of THz frequency electromagnetic waves characteristic of a plurality of pathogens into a library, index or database, wherein said library, index or database is used for identification of a specific pathogen in a living body.

Example 85. The method according to example 59, further comprising a step of imaging at least a portion of said living body by scanning of THz frequencies.

Example 86. The method according to example 1, further comprising a step of detecting resonance features of hydrogen bonds characteristic of said pathogen.

Example 87. A method for detecting a cancerous cell in a biopsy sample using electromagnetic waves within the terahertz (THz) range, wherein said method comprises steps of:
  a. obtaining a THz detection system (TDS);
  b. detecting a signal, within the Terahertz frequency range, specific to said cancerous cell; and,
  c. defining at least one characteristic of said cancerous cell within said biopsy according to said signal.

Example 88. The method according to example 87, wherein said characteristic is at least one of presence, absence, concentration, cell type, differentiation stage and metastatic profile.

Example 89. The method according to example 87, further comprising a step of detecting said signal passively.

Example 90. The method according to example 87, further comprising a step of generating predetermined THz frequency electromagnetic waves specific to resonate with said cancerous cell.

The present invention, in some embodiments thereof, provides methods and systems for detection of a pathogen, as the 2019 coronavirus or Ebola Virus, or any pandemic threat causing virus in a living body, as well as a cancerous cell or a contaminant, using electromagnetic waves within 0.1-20000 HZ and the terahertz (THz) range, comprising (a) obtaining a. detection system, or b. THz detection system (TDS); (c) detecting a signal emanating from the pathogen, cancerous cell or contaminant, within the Hertz or Terahertz frequency range; and, defining at least one characteristic of the pathogen, cancerous cell or contaminant according to the signal.

Additional Examples

Additional Example 1. A non-invasive method for detection of a pathogen in a living body using electromagnetic waves within the terahertz (THz) range, wherein said method comprises steps of:
 a. obtaining a THz detection system (TDS);
 b. detecting a signal emanating from said pathogen in or on said living body, within the Terahertz frequency range; and,
 c. defining at least one characteristic of said pathogen in or on said living body according to said signal.

Additional Example 2. The method according to Additional Example 1, wherein said characteristic is at least one of presence, absence, concentration and type or serotype.

Additional Example 3. Predetermined THz frequency electromagnetic waves specific to resonate with said pathogen.

Additional Example 4. The method according to Additional Example 1, further comprising a step of directing said waves to said living body to induce a detectable resonant signal from said pathogen.

Additional Example 5. The method according to Additional Example 1, further comprising a step of detecting a first electromagnetic wave fingerprint reflected from, or penetrating into or transmitted through said living body which is distinguishable from a second electromagnetic wave fingerprint reflected from or penetrating into or transmitted through a healthy living body.

Additional Example 6. The method according to Additional Example 5, further comprising a step of calculating the difference between said first electromagnetic wave fingerprint and said second electromagnetic wave fingerprint.

Additional Example 7. The method according to Additional Example 6, further comprising a step of defining at least one characteristic of said pathogen according to a predetermined significance of said difference by applying predetermined parameters or rules.

Additional Example 8. The method according to Additional Example 1, further comprising a step of directing electromagnetic waves having a frequency equal to the characteristic frequency of said pathogen so as to detect resonant vibration features of said pathogen.

Additional Example 9. The method according to Additional Example 1, further comprising a step of detecting THz frequency electromagnetic waves within a range of frequencies selected from a group of frequencies consisting of:
 about 0.01 THz to about 20 terahertz;
 about 0.2 to about 2.2 THz (10 to 79.2 cm-1);
 about 0.2 THz to about 30 THz; and
 about 800 THz to about 1200 THz.

Additional Example 10. The method according to Additional Example 1, further comprising a step of detecting THz frequency electromagnetic waves in a range of wavelengths selected from a group of wavelength ranges consisting of:
 between about 3 cm and about 3 µm; and
 about 2 cm-1 to about 300 cm-1.

Additional Example 11. The method according to Additional Example 1, further comprising a step of detecting predetermined electromagnetic waves in the range of sub THz frequency.

Additional Example 12. The method according to Additional Example 1, especially adapted for screening and/or detecting pandemic causing pathogens in airport gateways.

Additional Example 13. The method according to Additional Example 1, further comprising a step of detecting a signal reflected from, penetrating into or transmitted through said living body.

Additional Example 14. The method according to Additional Example 1, further comprising a step of detecting a parameter of said signal, said parameter is at least one selected from a group consisting of diffusion, absorption, polarization and chirality.

Additional Example 15. The method according to Additional Example 1, further comprising a step of collecting a plurality of THz frequency electromagnetic waves characteristic of a plurality of pathogens into a library, index or database, wherein said library, index or database is used for identification of a specific pathogen in a living body.

Additional Example 16. The method according to Additional Example 1, further comprising a step of imaging at least a portion of said living body by scanning of THz frequencies.

Additional Example 17. The method according to Additional Example 1, further comprising a step of detecting resonance features of hydrogen bonds characteristic of said pathogen.

Additional Example 18. A method for detecting a cancerous cell in a biopsy sample using electromagnetic waves within the terahertz (THz) range, wherein said method comprises steps of:
 a. obtaining a THz detection system (TDS);
 b. detecting a signal, within the Terahertz frequency range, specific to said cancerous cell; and,
 c. defining at least one characteristic of said cancerous cell within said biopsy according to said signal.

Additional Example 19. The method according to Additional Example 18, wherein said characteristic is at least one of presence, absence, concentration, cell type, differentiation stage and metastatic profile.

Additional Example 20. The method according to Additional Example 18, further comprising a step of generating predetermined THz frequency electromagnetic waves specific to resonate with said cancerous cell.

An Overview of Some Example Embodiments

An aspect of some embodiments relate to detecting pathogens such as, by way of a non-limiting example, viruses such as the coronavirus or Covid-19 virus, by irradiating a subject's body at one or more specific frequencies, and measuring conductance of the subject's body.

In some embodiments, the irradiation is optionally performed by a device designed for irradiating a first one of the subject's hands, and measuring conductivity from the first hand to the second hand.

In some embodiments, the irradiation is optionally performed at one or more specific frequencies associated with a specific target pathogen.

In some embodiments, a specific change in subject body conductance between a first measurement made prior to irradiation and a second measurement made during irradiation indicates presence of a pathogen associated with one or more of the specific frequencies used in the irradiation.

In some embodiments, a specific change in subject body conductance between a first measurement made prior to irradiation and a second measurement made after irradiation indicates presence of a pathogen associated with one or more of the specific frequencies used in the irradiation.

An aspect of some embodiments relates to detecting pathogens such as, by way of a non-limiting example, viruses such as the coronavirus or Covid-19 virus, by measuring conductance of a subject's body when the subject is holding a specific material associated with a pathogen. By way of a non-limiting example, holding.

In some embodiments, a way of introducing resonance into the system, and/or getting impedance or conductivity to change is by using parts of a pathogen or virus. A whole, weakened virus may be kept hermetically closed, or a protein or RNA parts of the pathogen or virus, that produce their own specific frequencies.

By way of a non-limiting example, in some embodiments, the recombinant 3C-1 protease enzyme is optionally used.

In some embodiments, a subject holds or put his palm on a pad which contains a sample of a virus or components of the virus.

In some embodiments, a specific change in subject body conductance between a first measurement made prior to holding the virus sample and a second measurement made after or during holding the virus sample indicates presence of a pathogen associated with the virus or components of the virus.

An aspect of some embodiments relates to detecting pathogens in a fluid sample, such as, by way of a non-limiting example, viruses such as the coronavirus or Covid-19 virus, by measuring baseline conductance of a specific device without the fluid sample, and comparing to conductance of the device in presence of the fluid sample.

In some embodiments, the fluid sample may be a subject's saliva sample.

In some embodiments, the specific device includes a chip or a nano-chip that contains nano-wires and one or more sample materials of a target pathogen, such as virus parts. In some embodiments, the amount of the virus associated with the chip may be approximately 1 nano-drop of, by way of a non-limiting example, 3C-1 protease (recombinant) and/or spike protein. In some embodiments, the nano-drop may contain a concentration of approximately a nano-mol of 3C-1 protease (recombinant) and/or spike protein, or a concentration of approximately a nano-gram 3C-1 protease (recombinant) and/or spike protein per milliliter In some embodiments, a baseline conductivity of the chip, before placing a sample to be tested in contact with the chip, is known.

In some embodiments, a baseline conductivity of the chip is measured before placing a sample to be tested in contact with the chip.

In some embodiments, a sample of saliva, or buccal swab or nasal pharyngal sample of a subject to be tested is placed in contact with the chip. The sample potentially contains specific parts of the virus: for example: 3C-1 protease, whole viruses, and part of the virus secreted into the sample.

Next, the conductivity of the chip in presence of the sample is measured, producing a second measurement.

The baseline conductivity and the second measurement are compared.

In some embodiments, if the comparison shows a difference greater than a specific percentage, presence of the target pathogen in the sample is suspected or determined.

In some embodiments, if the comparison shows a difference in a specific percentage range, presence of the target pathogen in the sample is suspected or determined.

Description of Some Example Embodiments

Reference is now made to FIG. 1, which is an illustration of an example embodiment of the invention.

FIG. 1 is a simplified block diagram illustration of an object 100 accepting radiation of various frequency sources 101 102 103 104 105 106 107.

The number of frequencies is not limited to seven, as shown in FIG. 1.

In some embodiments, only one frequency source, for example source 101, may be used to irradiate the object 100 at one specific frequency.

In some embodiments, one frequency source, for example source 101, may be used to irradiate the object 100 at any one of several specific frequencies.

In some embodiments, more than one frequency source 101 may be used to irradiate the object 100, each one of the frequency sources 102 102 at one specific frequency.

In some embodiments, more than one frequency source 101 may be used to irradiate the object 100, each one of the frequency sources 102 102 at any one of several specific frequencies.

Some non-limiting examples of specific frequencies associated with specific pathogens include:

For the Coronavirus and/or SARS:

152.19, 155, 304.39, 309.89, 456.5, 464.89, 608.7, 619.89, 760.89, 774.79, 1217.5, 1239.7, 1369.59, 1394.7, 2435, 2479.5, 4870, 4959, 9740, and 9918 Hz (Hertz); and 152.19, 155, 304.39, 309.89, 456.5, 464.89, 608.7, 619.89, 760.89, 774.79, 1217.5, 1239.7, 1369.59, 1394.7, 2435, 2479.5, 4870, 4959, 9740, and 9918 KHz (KiloHertz).

For the Coronavirus:

145.9, 165.69, 291.69, 331.39, 437.6, 497.1, 583.5, 662.7, 1167, 1312.79, 1325.5, 1491.2, 2333.9, 2651, 4667.8, 5301.89, and 9335.6 Hz; and 145.9, 165.69, 291.69, 331.39, 437.6, 497.1, 583.5, 662.7, 1167, 1312.79, 1325.5, 1491.2, 2333.9, 2651, 4667.8, 5301.89, and 9335.6 KHz.

For Coronaviridae infections:

80, 350, 5750, 12930, 63470, 182500, 435290, 562500, 793500, 995750 Hz; and.

80, 350, 5750, 12930, 63470, 182500, 435290, 562500, 793500, 995750 KHz.

Some non-limiting examples of specific frequencies associated with specific pathogens include, for example, for the Coronavirus and/or SARS and/or Coronaviridae infections, frequencies in the terahertz range, for example in a range between 0.75 and 1.1 TeraHertz.

It is noted that is some embodiments, digits following the decimal point are may be rounded up or down, and that the frequency range may include from a whole number just below the exact frequency to the next whole number just above the exact frequency. For example: 464.89 may optionally include 464-465.

Additional specific frequencies associated with each specific virus and/or pathogen can be added in methods known in the art.

In some embodiments, 10-20 relevant frequencies are optionally irradiated simultaneously by 10-20 devices.

In some embodiments, all frequencies will be irradiated into one location, a pillow acceptor of the frequencies.

Figure 2A:
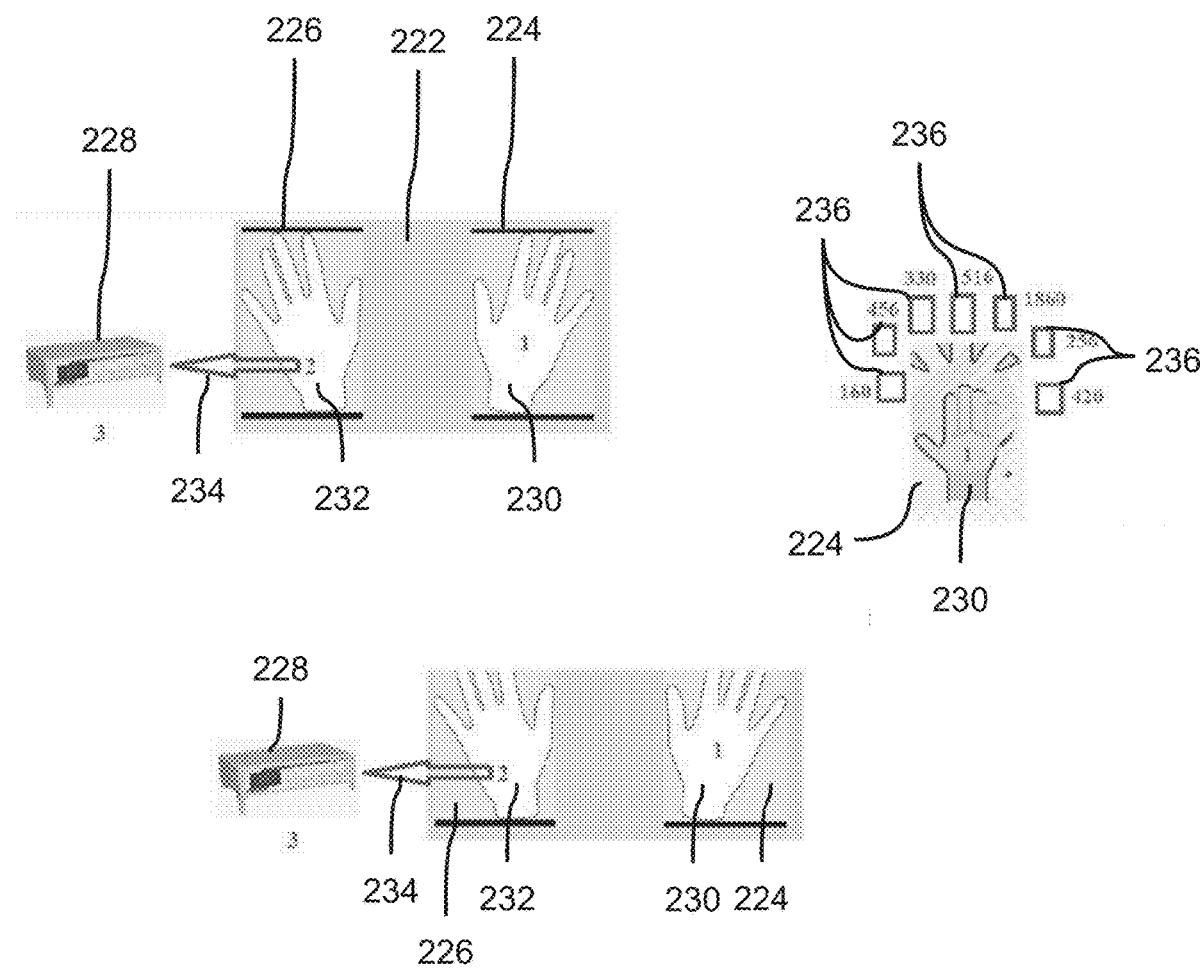
FIG. 2A is a simplified illustration of an example embodiment of the invention.

Reference is now made to FIG. 2A, which is a simplified illustration of an example embodiment of the invention.

FIG. 2A shows an example device used to implement an example method.

The example device includes an optional board 222; a first pad 224 for placing a first hand 230, for example a right hand 230, of a subject; a second pad 226 for placing a second hand 232, for example a left hand 232 of the subject; a conductance meter 228 for measuring conductance of the hand 232 on the second pad 226; and sources of irradiation 236 at various frequencies, some non-limiting examples of which are specified in FIG. 2A.

The example method includes:

a subject placing one hand 230 232 on each one of the pads 224 226;

measuring conductance of the left hand 232 by the conductance meter 228, producing a first conductance value;

irradiating the right hand 230 by radiation of one or more frequencies associated with a target pathogen such as the coronavirus. The radiation may optionally be simultaneous for all the frequencies;

measuring conductance of the left hand 232 by the conductance meter 228 again after irradiation, producing a second conductance value; and comparing a result of the second conductance value to the first conductance value.

In some embodiments, when the second conductance value is different by more than a threshold amount from the first conductance value, an alert is produced that the subject is carrying the target pathogen, for example the coronavirus.

In some embodiments, the threshold amount may be a reduction by approximately 30% of conductance.

In some embodiments, the target reduction in conductance is a reduction by a percentage in a range including from 5% to 100%.

In some embodiments, one or more of the first pad 224 and the second pad 226 is optionally configured to locate the subject's hand(s) so that contacts in the pad a located next to one or more meridians of the subject's hand(s).

Figure 2B:
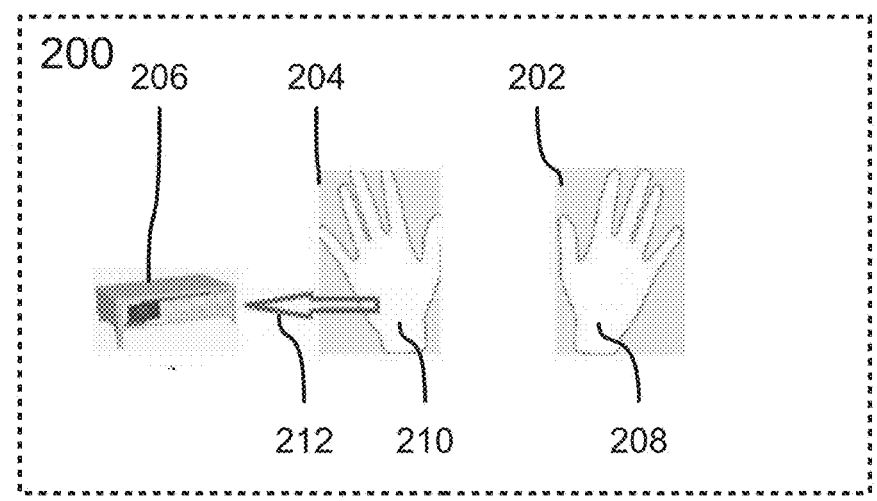
FIGS. 2B-2D are simplified illustrations of an example embodiment device in use according to an example embodiment method of the invention.
Figure 2C:
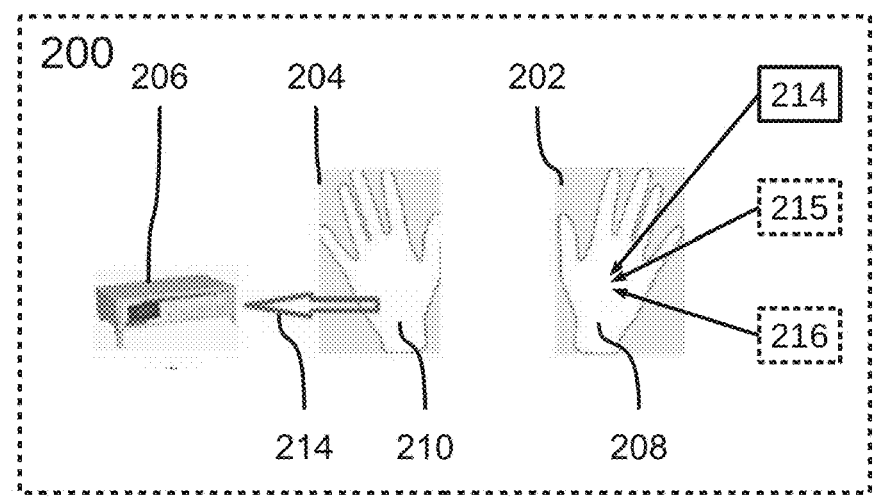
Figure 2D:
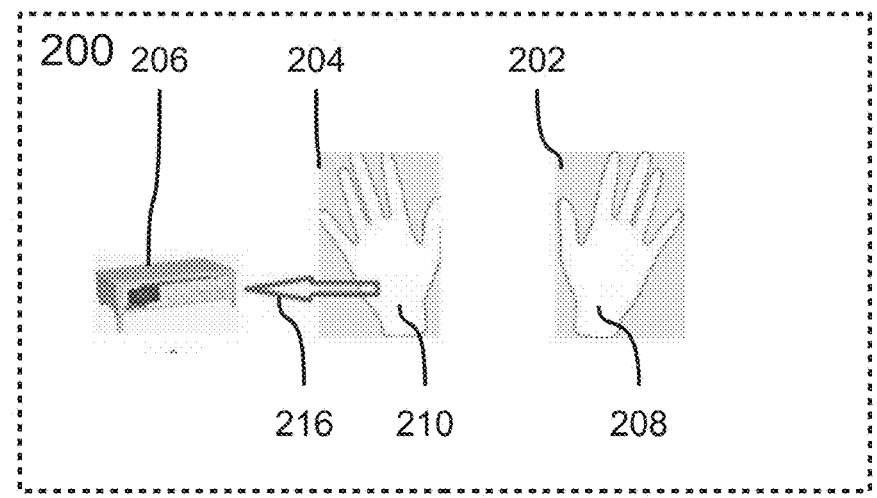

Reference is now made to FIGS. 2B-2D, which are simplified illustrations of an example embodiment device in use according to an example embodiment method of the invention.

FIG. 2B shows a simplified illustration of a non-limiting example embodiment of a device 200 for irradiating a subject's body at one or more specific frequencies, and measuring conductance of the subject's body.

The example device 200 of FIG. 2B includes a first pad 202 for a first subject body part 208—for example the subject's right hand 208; a second pad 204 for a second subject body part 210—for example the subject's left hand 210; and a conductance measuring device 206.

In some embodiments, the first pad 202 and the second pad 204 are optionally attached to, or constructed as parts of, a board which includes both of the first pad 202 and the second pad 204.

In some embodiments, one or more of the first pad 202 and the second pad 204 is optionally configured to locate the subject's hand(s) so that contacts in the pad a located next to one or more meridians of the subject's hand(s).

FIGS. 2B-2D show a simplified illustration of an example method of using the example device, which includes:

placing the right hand 208 on the first pad 202 and the left hand 210 on the left pad 204;

measuring 212 a first conductivity measurement at the left hand 210;

irradiating the right hand 208 by one or more irradiation sources 214 215 216 at one or more frequencies associated with a target pathogen such as the Coronavirus; and measuring 214 216 a second conductivity measurement at the left hand 210.

Measuring conductivity before and after irradiation is believed to detect effect of a virus in the subject's body resonating to one or more of the various irradiation frequencies. If a virus exists in the subject body, the virus is believed to resonate with the one or more of the various irradiation frequencies.

If the second conductivity measurement is lower than the first conductivity measurement by a specific threshold, the method optionally includes determining that the subject carries the target pathogen.

In some embodiments, the reduction in conductivity is a reduction by approximately 30%.

In some embodiments, the target reduction in conductance is a reduction by a percentage in a range including from 5% to 100%.

In some embodiments, the second measurement 214 is made during the irradiating.

In some embodiments, the second measurement 216 is made after the irradiating.

In some embodiments, measuring 212 214 216 conductivity at the left hand 210 is performed by measuring 212 214 216 conductivity at the left hand 210, optionally between two or more locations of the left hand 210.

In some embodiments, measuring 212 214 216 conductivity at the left hand 210 is performed by measuring conductivity between the right hand 208 and the left hand 210, optionally between a location at the right hand 208 and a location at the left hand 210.

In some embodiments, a device such as described above is optionally placed at airports and/or transportation hubs, for rapid screening of pathogen-carrying persons.

In some embodiments, results—whether the person is indicated to carry the pathogen or not, are optionally obtained in less than 30 seconds. In some embodiments, the results are optionally obtained in a duration range from 1 second to 1 minute.

Reference is now made to FIG. 2E, which is a simplified flow chart illustration of a method for detecting presence of coronavirus in a subject according to an example embodiment.

The method of FIG. 2E includes:

providing a baseline value of conductance of a subject's body (252);

irradiating the subject's body with electromagnetic radiation at frequencies associated with the coronavirus (254);

measuring the conductance of the subject's body, thereby providing a second value of conductance (256);

comparing the second value to the baseline value (258); and if the second value is different from the baseline value by more than a threshold amount, producing an alert that the subject's body carries the coronavirus (260).

In some embodiments, resonance is introduced to a conductivity measurement system, and impedance or conductivity change is optionally measured, by using a virus or the parts of a virus. In some embodiments, a whole, weakened virus is optionally kept hermetically closed, and/or a protein or RNA parts of the virus are kept, that produce their own specific frequencies.

In some embodiments, recombinant 3C-1 protease enzyme is used in an example embodiment method as described herein.

In some embodiments, an example screening method for detecting a pathogen or virus is used, which bears some similarity to the method described above with reference to FIGS. 2A-2D. Instead of irradiating specific frequencies, a subject holds or put his palm on a pad which contains the virus or part of virus particles.

An example method includes:
putting both palms on one or more conductivity pad(s);
measuring a baseline conductivity
holding a sample virus part, such as, by way of a non-limiting example, 3C-1 protease in one, first, hand.
repeating the conductivity measurement on another, second hand.

If a virus or part of virus exists in the subject's body, a change in conductivity is potentially measured.

It is noted that one can find 3C-1 protease secreted from the cells in a subject which carries the virus, such as, for example the SARS virus, The Covid-2 virus, and various other corona viruses.

It is noted that various methods of measuring a change of impedance and/or conductivity and/or muscle tonus, optionally even kinesiology methods, may optionally be used in a method as described above, by measuring an impact of a pathogen on body muscles or cells due to resonance.

An aspect of some embodiments relates to detecting pathogens in a fluid sample, such as, by way of a non-limiting example, viruses such as the coronavirus or Covid-19 virus, by measuring baseline conductance of a specific device without the fluid sample, and comparing to conductance of the device in presence of the fluid sample.

Figure 3A:
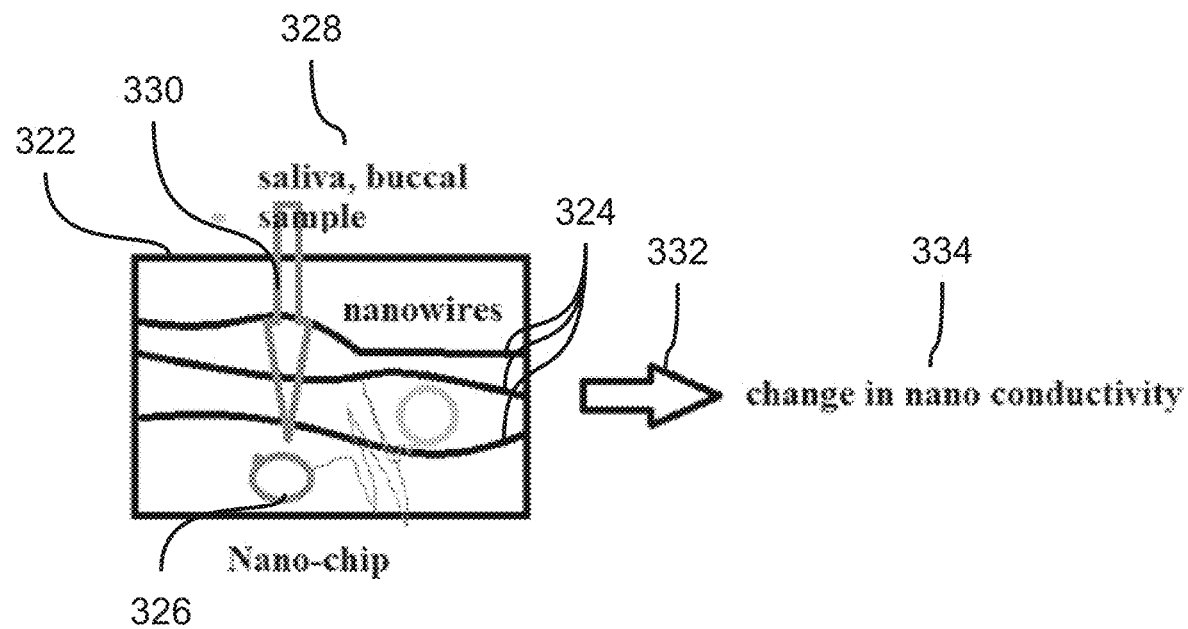
FIG. 3A is a simplified illustration of an example embodiment of the invention.

Reference is now made to FIG. 3A, which is a simplified illustration of an example embodiment of the invention.

FIG. 3A shows an example device used to implement an example method.

The example device includes a chip 322 or nano-chip 322, including wires 324 or nano-wires 324 between which conductance or impedance can optionally be measured.

FIG. 3A shows the chip 322 has deposited upon it material 326 associated with a target pathogen.

In some embodiments, the target pathogen may be, by way of a non-limiting example, the coronavirus or Covid-19 virus.

In some embodiments, the material 326 may include one or more whole, weakened viruses, or a protein or RNA parts of the pathogen or virus.

In some embodiments, a baseline value of conductance of the chip, by way of a non-limiting example conductance or impedance as measured between the wires 324, before placing a sample to be tested in contact with the chip, is known.

In some embodiments, a baseline value of conductance of the chip, by way of a non-limiting example conductance or impedance as measured between the wires 324, is measured before placing a sample to be tested in contact with the chip.

The example method includes:
providing 330 a sample 328 taken from a subject, such as, by way of a non-limiting example, saliva and/or a buccal sample;
placing the sample 328 in contact with the wires 324 on the chip 322;
measuring a value of conductance between the wires 324, thereby producing sample conductance value; and
comparing the sample conductance value to the baseline conductance value.

In some embodiments, when the sample conductance value is different by more than a threshold amount from the baseline conductance value, an alert is produced that the subject is carrying the target pathogen, for example the coronavirus.

In some embodiments, the threshold amount may be a reduction by 30% of conductance.

In some embodiments, the threshold amount may be a reduction by a percentage in a range including from 5% to 100% of conductance.

Figure 3B:
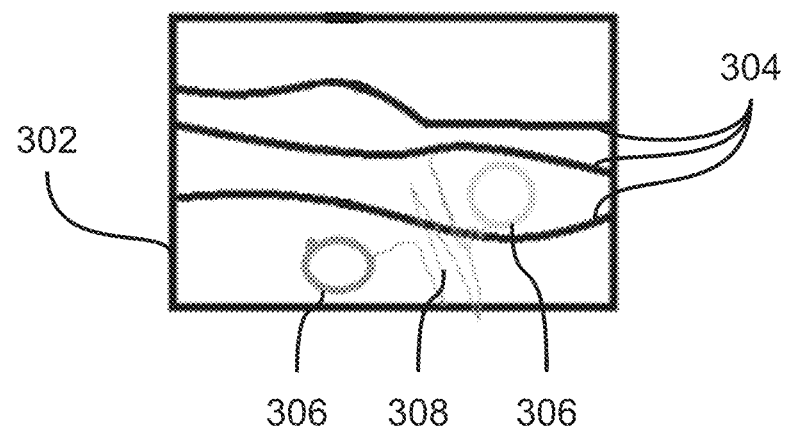
FIGS. 3B-3C are simplified illustrations of an example embodiment device in use according to an example embodiment method of the invention.
Figure 3C:
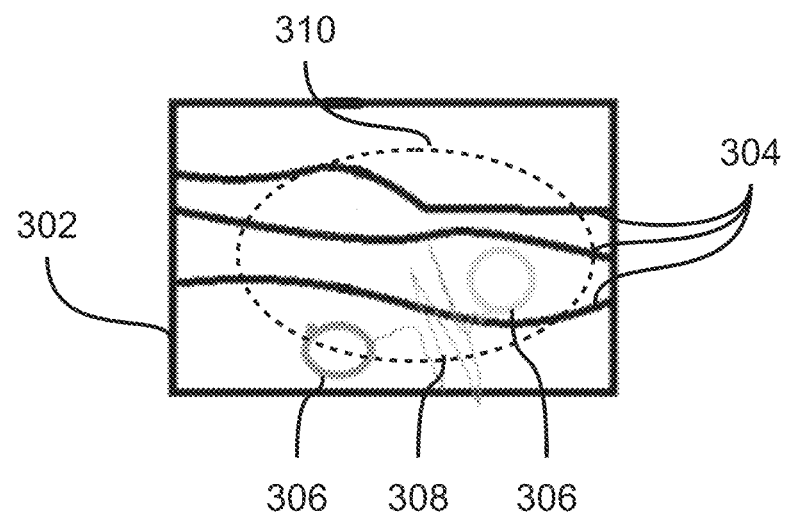

Reference is now made to FIGS. 3B-3C, which are simplified illustrations of an example embodiment device in use according to an example embodiment method of the invention.

FIG. 3B shows a simplified illustration of a non-limiting example embodiment of a chip 302 or nano-chip 302, including wires 304 or nano-wires 304 between which conductance or impedance can optionally be measured.

FIG. 3B shows the chip 302 has deposited upon it material 306 308 associated with a target pathogen.

In some embodiments, the target pathogen may be, by way of a non-limiting example, the coronavirus or Covid-19 virus.

In some embodiments, the material 306 308 may include one or more whole, weakened viruses 306, or a protein or RNA parts 308 of the pathogen or virus.

In some embodiments, a baseline value of conductance of the chip, by way of a non-limiting example conductance or impedance as measured between the wires 304, before placing a sample to be tested in contact with the chip, is known.

In some embodiments, a baseline value of conductance of the chip, by way of a non-limiting example conductance or impedance as measured between the wires 304, is measured before placing a sample to be tested in contact with the chip.

FIG. 3C shows the simplified illustration of the chip 302 of FIG. 3B, to which a sample specimen or drop or nano-drop 310 has been added.

Conductance or impedance as measured between the wires 304, is again measured, producing a second value.

The baseline value and the second value are compared, producing, by way of a non-limiting example, a ratio of the baseline value and the second value, or a percentage difference value of the baseline value and the second value.

In some embodiments, when the ratio of the baseline value to the second value is greater than a specific threshold, the sample is suspected or determined to include the target pathogen.

In some embodiments, when the ratio of the baseline value to the second value is within a specific range, the sample is suspected or determined to include the target pathogen.

In some embodiments, the fluid sample may be a subject's saliva sample, or buccal swab or nasal pharyngal sample.

In some embodiments, the material 306 308 associated with the target pathogen may optionally include, by way of a non-limiting example, one or more of virus parts, 3C-1 protease (recombinant) and/or spike protein.

In some embodiments, a non-limiting example method optionally includes: First step, a sample of saliva, or buccal swab or nasal pharyngal sample of the person to be tested is placed in a tube with a reaction mixture. The sample contains specific parts of the virus: for example: 3C-1 protease, Whole virus, any part of the virus secreted into the media.

Second step introducing a reaction vessel. The reaction vessel includes a chip—nano-chip that contains nano-wires and one or more virus parts. Range of (1 nano-drop). For example: 3C-1 protease (recombinant), spike protein.

Third step: a nano-drop of the reaction mixture is poured on the reaction vessel.

Fourth step: The chip is connected to a conductometer or impedance reader. Any change in conductivity is caused by the resonance between the components in the reaction mixture and the components of the nano bio chip.

Reference is now made to FIG. 4, which is a simplified flow chart illustration of a method for detecting presence of coronavirus in a subject according to an example embodiment.

The method of FIG. 4 includes:

providing a system (402), the system comprising:

a chip with a plurality of wires disposed on or in the chip;

a conductance meter arranged to measure conductance between the wires; and biological material associated with the coronavirus disposed on or in the chip providing a baseline value of conductance between wires in the chip (404);

providing a fluid sample taken from a subject (406);

disposing the fluid sample in upon the chip (408);

measuring conductance between the wires, producing a sampled value of conductance between wires in the chip (410);

comparing the sampled value to the baseline value (412);

if the sampled value is different from the baseline value by more than a threshold amount, producing an alert that the subject's body carries the coronavirus (414).

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for detecting presence of coronavirus in a subject, the method comprising:

providing a baseline value of conductance of the subject's body;

irradiating the subject's body with electromagnetic radiation at a frequency associated with the coronavirus, wherein the frequency is selected from a group consisting of:

182500 KHz;
435290 KHz;
562500 KHz;
793500 KHz; and
995750 KHz;
measuring the conductance of the subject's body, thereby providing a second value of conductance;
comparing the second value to the baseline value; and
producing an alert that the subject's body carries the coronavirus where the second value is different from the baseline value by more than a threshold amount.

2. The method according to claim 1, wherein the irradiating comprises irradiating at a plurality of frequencies associated with the coronavirus and selected from the group consisting of:
182500 KHz;
435290 KHz;
562500 KHz;
793500 KHz; and
995750 KHz.

3. The method according to claim 2, wherein the irradiating comprises irradiating at the plurality of frequencies simultaneously.

4. The method according to claim 1, wherein the measuring the conductance of the subject's body comprises measuring the conductance during the irradiating the subject's body with the electromagnetic radiation.

5. The method according to claim 1, wherein the measuring the conductance of the subject's body comprises measuring the conductance after the irradiating the subject's body with the electromagnetic radiation.

6. The method according to claim 1, wherein the irradiating the subject's body comprises irradiating a left hand and the measuring the conductance of the subject's body comprises measuring the conductance at the right hand.

7. The method according to claim 1, wherein the irradiating the subject's body comprises irradiating a first hand, and the measuring the conductance of the subject's body comprises measuring the conductance for a meridian measurement, wherein the meridian measurement is the junction between the palm and the first hand.

8. The method according to claim 1, wherein the irradiating the subject's body comprises irradiating a first hand, and the measuring the conductance of the subject's body comprises measuring the conductance from the first irradiated hand to a second hand.

9. The method according to claim 1, wherein the irradiating the subject's body comprises irradiating a first hand, and the measuring the conductance of the subject's body comprises measuring conductance from a meridian on the irradiated first hand to a meridian on a second hand.

10. The method according to claim 1, wherein the threshold amount is approximately a 30% reduction of conductance.

* * * * *